(12) United States Patent
Johnson et al.

(10) Patent No.: US 11,597,841 B2
(45) Date of Patent: *Mar. 7, 2023

(54) WAX-BASED COMPOSITIONS, ARTICLES MADE THEREFROM, AND METHODS OF MANUFACTURE AND USE

(71) Applicant: ULTRADENT PRODUCTS, INC., South Jordan, UT (US)

(72) Inventors: Steven B. Johnson, Magna, UT (US); David Lawrence Margetts, Salt Lake City, UT (US); Barry Lee Hobson, Grantsville, UT (US); Jonathan D. Scoville, Sandy, UT (US); Neil T. Jessop, Sandy, UT (US); Peter M. Allred, Bluffdale, UT (US); Dan E. Fischer, Sandy, UT (US)

(73) Assignee: ULTRADENT PRODUCTS, INC., South Jordan, UT (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/136,146

(22) Filed: Dec. 29, 2020

(65) Prior Publication Data

US 2021/0115254 A1      Apr. 22, 2021

Related U.S. Application Data

(63) Continuation of application No. 15/027,636, filed as application No. PCT/US2014/022053 on Mar. 7, 2014, now Pat. No. 10,913,853.

(Continued)

(51) Int. Cl.
*A61F 5/00* (2006.01)
*C08L 91/06* (2006.01)
(Continued)

(52) U.S. Cl.
CPC ............... *C08L 91/06* (2013.01); *A61C 7/08* (2013.01); *A61C 7/125* (2013.01); *A61C 19/05* (2013.01);
(Continued)

(58) Field of Classification Search
CPC .............. A61F 5/566; A61F 5/56; A61F 5/37; A61C 7/08; A61C 7/36; A61C 5/14; A63B 71/085
(Continued)

(56) References Cited

U.S. PATENT DOCUMENTS 2,298,846 A   10/1942  Skooglund
2,577,816 A   12/1951  Schneider et al.
(Continued)

FOREIGN PATENT DOCUMENTS

AU   2018232963 A1   10/2018
CA      2726043 A1   12/2009
(Continued)

OTHER PUBLICATIONS

"Parafilm(Registered) M Barrier Film", Aug. 11, 2010 (Aug. 11, 2010), p. 2, XP055333981.
(Continued)

*Primary Examiner* — Adam Baker
(74) *Attorney, Agent, or Firm* — Workman Nydegger

(57) ABSTRACT

Oral treatment devices formed from wax-based compositions that are thermally stable when formed into a three-dimensional shape to a temperature of at least 45° C. and plastically deformable at room temperature (25° C.). The wax-based compositions include a wax fraction homogeneously blended with a polymer fraction. The wax fraction includes at least one wax. The polymer fraction includes at least one polymer selected such that, when the wax and polymer are homogeneously blended together, they yield a
(Continued)

wax-based composition having the desired properties of thermal stability and plastic deformability. Oral treatment devices are dimensionally stable to a temperature of at least 40° C. without external support and can be plastically deformed in a user's mouth to become at least partially customized to the size and shape of user's unique dentition and/or an appliance in a user's mouth.

20 Claims, 14 Drawing Sheets

Related U.S. Application Data

(60) Provisional application No. 61/889,880, filed on Oct. 11, 2013.

(51) Int. Cl.
| | |
|---|---|
| *C08L 23/16* | (2006.01) |
| *A61C 19/06* | (2006.01) |
| *A61C 7/08* | (2006.01) |
| *A61C 7/12* | (2006.01) |
| *A61C 19/05* | (2006.01) |
| *A61F 5/56* | (2006.01) |
| *A61L 31/04* | (2006.01) |
| *A63B 71/08* | (2006.01) |
| *C08J 5/18* | (2006.01) |

(52) U.S. Cl.
CPC .......... *A61C 19/063* (2013.01); *A61C 19/066* (2013.01); *A61F 5/566* (2013.01); *A61L 31/041* (2013.01); *A63B 71/085* (2013.01); *C08J 5/18* (2013.01); *C08L 23/16* (2013.01); *A61F 2005/563* (2013.01); *C08J 2323/16* (2013.01); *C08J 2391/06* (2013.01); *C08L 2203/02* (2013.01); *C08L 2203/30* (2013.01)

(58) Field of Classification Search
USPC .... 128/848, 859, 861, 862; 433/5–8, 19, 24, 433/140
See application file for complete search history.

(56) References Cited

U.S. PATENT DOCUMENTS

| | | | |
|---|---|---|---|
| 2,582,037 A | 1/1952 | Hyde | |
| 2,707,951 A | 5/1955 | Shackelford | |
| 2,773,045 A | 12/1956 | Simerl et al. | |
| 3,326,835 A | 6/1967 | Signorelli et al. | |
| 3,745,033 A | 7/1973 | Hutchison | |
| 4,614,758 A | 9/1986 | Schwabe et al. | |
| 5,299,936 A | 4/1994 | Ueno | |
| 5,339,832 A | 8/1994 | Kittelsen et al. | |
| 5,810,961 A | 9/1998 | Andersen et al. | |
| 6,302,686 B1* | 10/2001 | Chott .................. | A61F 5/566 128/859 |
| 6,358,043 B1 | 3/2002 | Mottate et al. | |
| 6,629,841 B1 | 10/2003 | Skinner | |
| 7,625,210 B2 | 12/2009 | Allred et al. | |
| 7,645,137 B2 | 1/2010 | Wasyluch | |
| 7,775,214 B1* | 8/2010 | Lesniak .................. | A61F 5/566 128/846 |
| 7,959,902 B1 | 6/2011 | Postlewaite | |
| 8,113,837 B2 | 2/2012 | Zegarelli | |
| 8,277,215 B2 | 10/2012 | McLean et al. | |
| 8,357,795 B2 | 1/2013 | LeBreton | |
| 8,944,819 B2 | 2/2015 | Faasse et al. | |
| 8,956,160 B2 | 2/2015 | Willison et al. | |
| 9,789,036 B2 | 10/2017 | Jensen | |
| 10,646,318 B2* | 5/2020 | Johnson .................. | A61P 1/02 |
| 10,913,853 B2* | 2/2021 | Johnson .................. | C08L 91/06 |
| 2003/0075184 A1 | 4/2003 | Persichetti | |
| 2003/0088011 A1 | 5/2003 | Kamohara et al. | |
| 2003/0205234 A1 | 11/2003 | Bardach et al. | |
| 2004/0005277 A1 | 1/2004 | Willison et al. | |
| 2004/0038171 A1 | 2/2004 | Jacobs et al. | |
| 2005/0260544 A1 | 11/2005 | Jones et al. | |
| 2006/0233865 A1 | 10/2006 | Odajima et al. | |
| 2007/0298380 A1 | 12/2007 | Allred | |
| 2008/0081852 A1 | 4/2008 | Kamohara et al. | |
| 2009/0305184 A1 | 12/2009 | Ting et al. | |
| 2010/0028829 A1 | 2/2010 | Lewis et al. | |
| 2010/0112510 A1 | 5/2010 | Wasylucha | |
| 2010/0269836 A1 | 10/2010 | Roettger et al. | |
| 2011/0171066 A1 | 7/2011 | Captain et al. | |
| 2011/0171605 A1 | 7/2011 | McLlean et al. | |
| 2011/0171606 A1 | 7/2011 | Lewis et al. | |
| 2011/0189637 A1 | 8/2011 | Andersen | |
| 2011/0207087 A1 | 8/2011 | Jones et al. | |
| 2012/0214904 A1 | 8/2012 | Prusty et al. | |
| 2012/0325224 A1 | 12/2012 | Elkin et al. | |
| 2013/0184390 A1 | 7/2013 | Bhakta et al. | |
| 2013/0298916 A1 | 11/2013 | Alvarez et al. | |
| 2014/0196725 A1 | 7/2014 | Maurello | |
| 2014/0335467 A1 | 11/2014 | Yamamoto et al. | |
| 2015/0374464 A1 | 12/2015 | Stewart | |
| 2016/0015496 A1 | 1/2016 | Johnson et al. | |
| 2016/0230007 A1 | 8/2016 | Johnson et al. | |
| 2022/0117865 A1 | 4/2022 | Sagel et al. | |

FOREIGN PATENT DOCUMENTS

| | | |
|---|---|---|
| CN | 85101852 A | 1/1987 |
| CN | 1343109 A | 4/2002 |
| CN | 1708382 A | 12/2005 |
| CN | 1791368 A | 6/2006 |
| CN | 1913867 A | 2/2007 |
| CN | 201147381 Y | 11/2008 |
| CN | 101869510 A | 10/2010 |
| CN | 101909582 A | 12/2010 |
| CN | 201692090 U | 1/2011 |
| GB | 0980405 A | 1/1965 |
| JP | 60-240762 A | 11/1985 |
| JP | 2003-019240 A | 1/2003 |
| JP | 2004-538085 A | 12/2004 |
| JP | 2009-084326 A | 4/2009 |
| JP | 2010-075644 A | 4/2010 |
| WO | 93/02860 A1 | 2/1993 |
| WO | 2006/050108 A1 | 5/2006 |
| WO | 2006/052593 A2 | 5/2006 |
| WO | 2012/081396 A1 | 6/2012 |
| WO | 2013/173100 A1 | 11/2013 |
| WO | 2014/138659 A2 | 9/2014 |

OTHER PUBLICATIONS

Anonymous: "Productinformation Sheet: Parafilm M—P 7793, P 7543 P 7668 and P 6543", Oct. 1, 2003, p. 1, XP055288857.
Engineers Handbook, "Engineering Materials—Thermoset Plastics—Silicone", retrieved from internet Jun. 22, 2017.
Mixture—definition of mixture in English_Oxford Dictionaries.
Star Thermoplastics, "Thermoplastic vs. Thermostet" retrieved from internet Jun. 22, 2017.
Conrad, Robin. "Styrene-Ethylene-Butylene-Styrene Thermoplastic Elastomer (SEBS)". Jun. 23, 2021. Accessed via elastomer.kuraray.com/us/blog/sebs/on Jun. 8, 2022 (Year: 2021).
ExxonMobil "Vistamaxx performance polymers". 2022. Accessed via https://www.exxonmobilchemical.com/en/products/polymer-modifiers/vistamaxx-perfomnance-polymerson Jun. 8, 2022 (Year: 2022).
Nevada State Athletic Commission "Mouth Guard Study". May 15, 2008. Accessed via boxing.nv.gov/uploadedFiles/boxingnvgov/content/HotTopics/MouthGuardStudy.pdf on Jun. 8, 2022 (Year: 2008).
Australian Office Action cited in Australian Application No. 2014225412 dated Jan. 5, 2018.
"EPO Extended Search Report cited in EP Application No. EP105485KG900pb dated Aug. 6, 2017."

(56) References Cited

OTHER PUBLICATIONS

Anonymous "Product Information Sheet Parafilm M—P7793, P 7543, P 7668 and P 6543" Oct. 1, 2003, 1 page.
Carey, Francis A., "Organic Chemistry" Second Edition, 1992.
Engineers Handbook, "Engineering Materials—Thermoset Plasitcs—Silicone", retreived from internet Jun. 22, 2017.
Final Office Action received for U.S. Appl. No. 15/027,636, dated Aug. 4, 2020, 16 pages.
International Search Report and Written Opinion for PCT/US2014/022053. dated Jul. 8, 2014.
International Search Report and Written Opinion issued in PCT Application No. PCT/US2014/022032 dated Aug. 27, 2014.
Office Action received for U.S. Appl. No. 14/772,967, dated Feb. 9, 2017.
Office Action received for U.S. Appl. No. 14/772,967, dated Jun. 28, 2017.
Office Action received for U.S. Appl. No. 14/772,967, dated Nov. 3, 2016.
Office Action received for U.S. Appl. No. 14/772,967, dated Sep. 3, 2019.
Star Thermoplastics, "Thermoplastic vs. Thermostet" retrived from internet Jun. 22, 2017.
Structure Probe Inc.: Parafilm M Barrier Film; Aug. 11, 2010, p. 2, paragraph 7.
Wikipedia Definition of Polymer; downloaded May 24, 2018.

\* cited by examiner

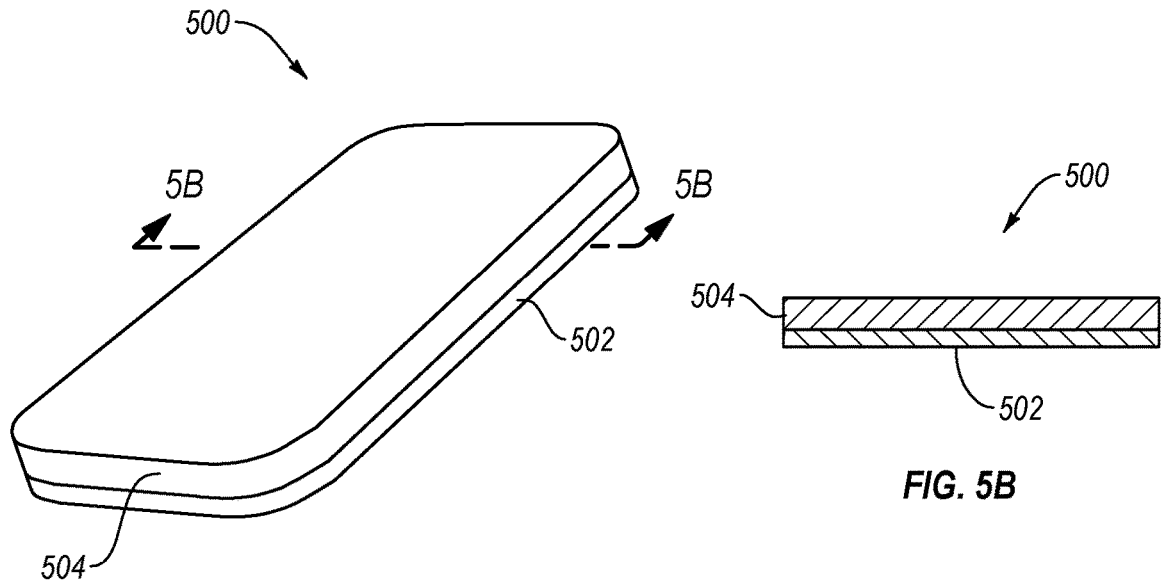
FIG. 5A
FIG. 5B
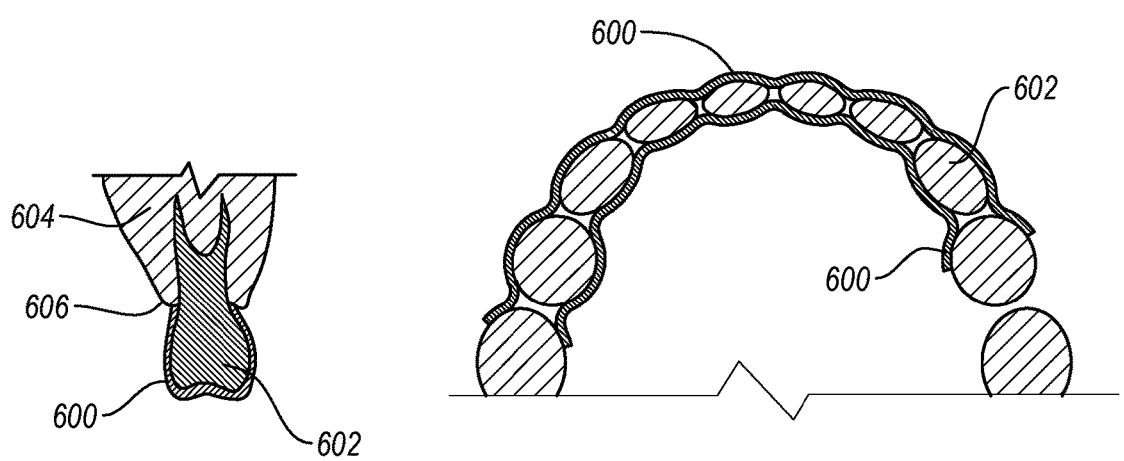
FIG. 6A
FIG. 6B

WAX-BASED COMPOSITIONS, ARTICLES MADE THEREFROM, AND METHODS OF MANUFACTURE AND USE

CROSS REFERENCE TO RELATED APPLICATIONS

This application is a continuation of U.S. patent application Ser. No. 15/027,636, filed Apr. 6, 2016, which is a 371 application of International Patent Application No. PCT/US2014/022053, filed Mar. 7, 2014, which claims the benefit of U.S. Provisional Application No. 61/889,880, filed Oct. 11, 2013, which are incorporated by reference in their entirety.

BACKGROUND OF THE INVENTION

1. The Field of the Invention

The present invention is in the field of wax-based compositions, barrier layers, and oral treatment devices and other articles made from such compositions, and methods for making and using the foregoing.

2. The Relevant Technology

Dental treatment trays and strips are commonly used to deliver bleaching compositions and medicaments to a user's teeth. "Trays" are pre-shaped barriers designed to fit over some or all of a user's teeth and can be customized or non-customized. Trays can be pre-loaded with an oral treatment composition or filled with a treatment composition by the user at the time of use. "Strips" are generally non-customized sheet-like barriers that include a treatment composition on one side or embedded within the barrier layer and which can be placed over and folded around a user's teeth in a tray-like configuration.

One type of customized dental tray is made by thermoforming a sheet of moisture-resistant thermoplastic polymer material, such as ethylene vinyl acetate copolymer (EVA), over a stone model of a user's teeth and then trimming the intermediate molded form to yield the desired tray-like shape. A block-out material can be applied to the stone model to form reservoirs in the customized tray, which can accommodate placement of additional treatment composition next to a person's tooth surfaces. Reservoirs can provide additional comfort by reducing orthodontic forces, particular with more rigid trays. Drawbacks of customized trays formed in this manner include the time and cost of forming an impression of a person's teeth, typically at a dentist office, using the impression to form the stone model, thermoforming the sheet, and trimming the molded form to yield the customized tray. The main benefit is that such trays typically provide the best fit, comfort and effectiveness in delivering a medicament to a user's teeth as compared to oral strips and other types of dental trays.

Another type of customized tray is made using a person's own teeth as the template (e.g., so called "boil-and-bite" trays). In a typical customization process a non-customized tray blank made from a thermally softenable polymer material is initially heated (e.g., in hot water or microwave oven) to temporarily soften the polymer tray material. The softened tray is then placed over the user's teeth and custom-formed to the user's teeth using forces applied by one or more of biting, suctioning, or externally applied pressure using fingers. When the customized tray has cooled sufficiently to retain its form, it can be removed from the user's mouth and is then ready for use. A drawback of self-customized trays is that they can be bulky and uncomfortable, particularly when in the form of sports mouth guard, which typically have a wall thickness of at least 3 mm and usually more. And while there have been patents directed to thin-walled, self-customizable trays, such trays can be difficult for a non-dental practitioner to use, have poor fit, and have had little market acceptance.

Non-customized trays lack features corresponding to a user's unique dentition but can be made to roughly approximate the size and shape of a variety of differently sized and shaped dental arches. A major drawback of non-customized trays is poor fit. Thicker walled trays can be bulky, uncomfortable and often have large gaps between the side walls and the user's tooth surfaces. Thinner, more flexible trays can better adapt to the shape of a user's teeth but have their own drawbacks. The thinnest and most comfortable of such trays can be flimsy and difficult to install and are more easily dislodged during use compared to custom-fitted trays or more rigid non-customized trays. Thin-walled trays made from materials that are sufficiently rigid and/or resilient so as to better maintain their tray-like shape and facilitate installation over a user's teeth tray are less adaptable and have tray walls that are more likely to pull away from a user's teeth during use, particularly the lingual wall. This can be both annoying to the user and permit ingress of saliva into the trough, which can cause diffusion of treatment composition into the person's oral cavity.

Conventional dental treatment strips typically comprise a flexible plastic barrier layer coated or impregnated with a treatment composition on the side of the strip facing the user's teeth. To install the strip, a portion of the strip is placed over the front surfaces of the user's teeth and the remainder is folded around the occlusal edges of the teeth and against the lingual surfaces. A drawback of strips is that they are generally more difficult to install over a user's teeth in the proper location compared to trays, which already have a trough into which the teeth are to be placed, which directs correct installation. Nevertheless, a properly placed strip can remain in place and provide a high level of comfort during treatment, perhaps even more comfort than a dental tray. An improperly placed strip, however, can fail to properly cover all tooth surface to be treated, may require adjustment, and can permit treatment composition to rapidly diffuse into the user's oral cavity. Moreover, strips with less adhesive treatment compositions are prone to slip off the teeth during use as a result of even minimal movement of the user's mouth, jaw or tongue. It is usually recommended that users not eat, drink, smoke or sleep while wearing the treatment strip. In some cases, the strip can become so dislodged or mangled that it must be removed and replaced with a fresh strip to complete the desired treatment.

Ultimately, the main impediment to successful treatment is the failure of a user to complete the prescribed treatment regimen. If the treatment apparatus is uncomfortable to wear, difficult to install and/or is prone to prematurely dislodge from the user's teeth, the user may simply give up and prematurely abort the prescribed regimen. Thus, even if dental treatments are possible using a particular treatment apparatus or method, they are less likely to be properly completed if the inadequacies of the treatment apparatus or method cause a user to become discouraged before the desired results are attained.

BRIEF SUMMARY

Disclosed herein are wax-based compositions suitable for making sheets or articles that are thermally stable and plastically deformable. Example wax-based compositions include a wax fraction comprised of at least one wax and a polymer fraction homogeneously blended with the wax fraction comprised of at least one polymer. According to one embodiment, the wax-based composition is plastically deformable at room temperature (25° C.) and thermally stable when formed into a flat sheet or three-dimensional article to a temperature of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70° C.

Also disclosed is a method of manufacturing a wax-based composition that is suitable for making sheets or articles that are thermally stable and plastically deformable, wherein the method comprises: (1) combining a least one wax and at least one polymer to form a mixture; and (2) processing the mixture to form a wax-based composition (a) that is comprised of a wax fraction homogeneously blended with a polymer fraction, (b) that is thermally stable when formed into a flat sheet or three-dimensional article to a temperature of at least 45° C., and (c) that is plastically deformable at room temperature (25° C.).

Flat sheets and three-dimensional articles made from wax-based compositions as disclosed herein can be used for any desired use, an example of which is as a barrier layer forming part on oral treatment device. According to one embodiment, the barrier layer can be in the form of a dental treatment tray having at least one side wall and at least one bottom wall extending laterally from the at least one side wall. According to another embodiment, the barrier layer can be in the form of a strip. The oral treatment devices include an oral treatment composition that includes one or more active agents for providing a desired oral treatment.

According to one embodiment, barrier layers made from wax-based compositions are non-customized and devoid of features corresponding to user's unique dentition. Because of the unique properties of wax-based compositions disclosed herein, the barrier can be at least partially customizable when placed into the user's mouth and heated to body temperature so as to at least partially conform to the user's unique dentition, particularly the occlusal surfaces. In this way, the oral treatment device can be self-customized by a user during use. This eliminates the need to first perform a customization procedure prior to placing an oral treatment composition adjacent to the barrier layer in order to obtain a device that closely conforms to a user's unique dentition so as to function as an at least partially customized oral treatment device. And to the extent the wax-based composition forming the barrier layer is not elastic but is plastically deformable, once the tray is fitted over a user's teeth there is less likelihood that the barrier layer will pull away from the user's teeth, as often occurs in the case of flexible barrier layers made from a resilient and/or elastomeric material.

Other examples of articles made from wax-based compositions as disclosed herein include, but are not limited to, therapeutic delivery devices (e.g., trays or strips) used to deliver therapeutic agents day or night to geriatric patients, convalescent patients, patients with poor hygiene, intubated humans, or other patients to treat a variety of conditions, including dry mouth, infections, dental conditions, tooth sensitivity, and the like. Examples of active oral agents include, but are not limited to, fluoride, desensitizing agents, anesthetics, remineralizing agents, anti-plaque agents, anti-tartar agents, antimicrobial agents, antibiotics, chlorhexidine, doxycycline, or healing agents for soft oral tissues). The active oral agents can be contained within compositions of varying rheology, including but not limited to, sticky viscous compositions, substantially solid compositions, putty-like compositions, less viscous or fluid compositions. By way of example, a fluoride treatment composition can be a sticky viscous gel or, alternatively, may be a less viscous, more fluid composition that can be easily rinsed from a patient's teeth. Alternatively, a solid active agent (e.g., doxycycline or other antibiotic for treating periodontal pockets) can be embedded in a wall of a wax-based tray or strip and held against or near a region of oral tissue for prolonged treatment.

Therapeutic devices may include a barrier liner made from a wax-based composition and an oral treatment composition pre-loaded therein (e.g., a sticky, viscous composition, substantially solid composition, or putty-like material). Alternatively, therapeutic devices may include a barrier liner made from a wax-based composition and an absorbent insert or lining (e.g., absorbent paper or sponge material) that acts as a reservoir to retain more fluid, less viscous oral compositions within the tray and adjacent to teeth and/or oral tissues that might otherwise diffuse or be expressed from the device into the oral cavity in an undesired manner.

Other treatment devices include, but are not limited to, orthodontic guard devices (e.g., a tray or strip) to protect soft oral tissues from orthodontic devices that might cause irritation, particularly when first installed, including orthodontic guard trays and strips that can form a barrier between irritating features of an orthodontic device and soft oral tissues; devices for treating disorders of the temporomandibular joint ("TMJ") ("TMJ disorders" or "TMD"); anti-bruxing devices; customizable sports mouth guards, including customizable inserts for sports mouth guards and two-color molded sports mouth guards; deformable strips or sheets for registering occlusal points; and surgical trays designed to protect oral tissues after oral surgeries and/or deliver therapeutic agents.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIGS. 5A-5B illustrate an oral treatment device that includes a barrier layer in the form of an initially flat strip coated with an oral treatment composition;

FIGS. 6A-6B illustrate an oral treatment strip wrapped around and closely conforming to the shape of a user's teeth as a result of the highly adaptive nature of the wax-based barrier layer and adhesive nature of the oral treatment composition;

DETAILED DESCRIPTION OF THE PREFERRED EMBODIMENTS

I. Introduction

Figure 1A:
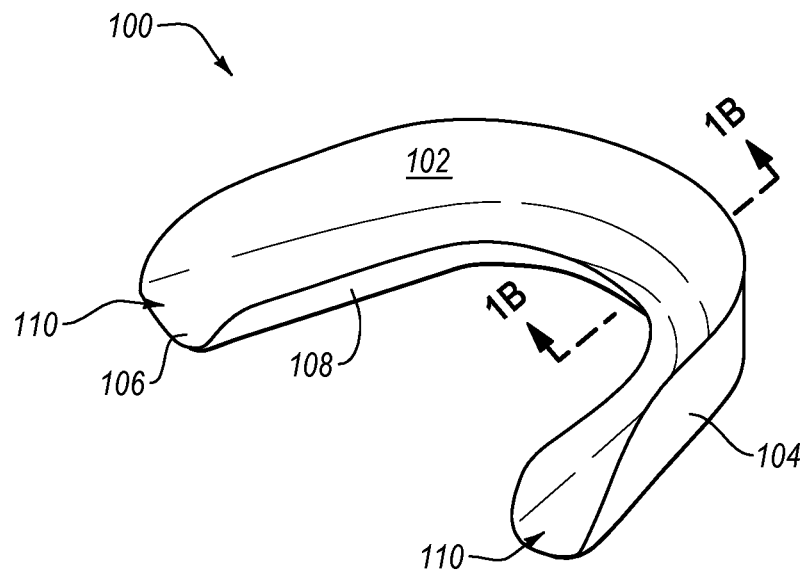
FIGS. 1A-1B illustrate exemplary oral treatment trays made from wax-based compositions as disclosed herein.

Disclosed herein are wax-based compositions formed from a wax component and a polymer component so as to be both thermally stable and plastically deformable. Because the wax-based compositions are thermally stable, articles made therefrom are able to maintain their shape without significant deformation (i.e., are dimensionally stable) in the absence of external forces when heated to temperatures at which such articles may be exposed. Because the wax-based compositions are plastically deformable, articles made therefrom are able to be plastically deformed by application of a deformation force.

Also disclosed are methods of manufacturing wax-based compositions from one more types of wax, one or more types of polymers, and optionally one or more auxiliary components so as to have desired materials and/or mechanical properties. The one or more types of wax and one or more types of polymers can be homogeneously blended together to form wax-based compositions containing a wax fraction and a polymer fraction. Heat and/or pressure can be applied to yield a wax-based composition having the desired materials and/or mechanical properties.

Example articles that can be made from wax-based compositions as disclosed herein include sheets and three-dimensional forms. The sheets and three-dimensional articles can be thermally stable and plastically deformable. The sheets can be used for any desired purpose, examples of which include as a barrier layer in an oral treatment strip used to apply an oral treatment composition to a user's teeth and/or gums, as an intermediate substrate that is thermo-formed into a dental treatment tray, and as a covering for reversibly sealing an orifice of a container. Examples of useful three-dimensional articles include dental treatment trays, such as those made by injection molding the wax-based composition or thermoforming a wax-based sheet.

Oral treatment devices are an example of a specific application of example articles made from wax-based compositions as disclosed herein. Oral treatment devices can include a barrier layer, such as a strip or tray, and one or more oral treatment compositions adjacent to and/or impregnated within the barrier layer. An example oral treatment strip includes a wax-based sheet that is initially flat and includes an oral treatment composition adjacent to and/or impregnated within the sheet. The oral treatment strip can be placed over and wrapped around at least a portion of a user's teeth. Another example of an oral treatment device includes a preformed dental treatment tray formed from a wax-based composition and an oral treatment composition placed and/or impregnated within the dental treatment tray. The pre-formed dental treatment tray facilitates greater ease of placement of the oral treatment device over a person's teeth compared to an oral treatment strip.

According to one embodiment, an oral treatment device includes a barrier layer that is initially non-customized and devoid of features corresponding to a user's unique dentition but which can adapt to the person's teeth during use. According to one embodiment, the barrier layer is at least partially customizable when warmed to body temperature and shaping forces are applied, such as suctioning, biting and/or finger pressure. In this way, a self-customizable oral treatment device is provided that can be self-customized in a user's mouth after placement of an oral treatment composition on or in the barrier layer. This greatly facilitates oral treatment because it provides a comfortable fitting, customized device that can be made during oral treatment. This eliminates cumbersome customization procedures and time delays typically involved in making customized trays, whether using a stone model of a person's teeth or in a "boil and bite" procedure. Customization has heretofore required customization prior to applying the oral treatment composition on or in a customized dental tray. The ability of oral treatment devices that already include a treatment composition to be self-customized in the user's mouth is surprising and unexpected, which further emphasizes the unique and inventive nature of wax-based compositions as disclosed herein.

Kits are also provided that utilize barrier layers made from wax-based compositions as disclosed herein and oral treatment devices that include barrier layers and one or more oral treatment compositions adjacent to or impregnated within the barrier layer. Kits may include multiple oral treatment devices that include a barrier layer and one or more pre-applied oral treatment compositions. Alternatively, kits may include one or more oral treatment devices that include a barrier layer and one or more oral treatment compositions that can be applied to the barrier layer by a user.

Methods of providing treatment to a user's teeth and/or gums utilize barrier layers made from wax-based compositions as disclosed herein and one or more oral treatment compositions that are pre-applied to the barrier layer or which can be applied to the barrier layer by a user at the time of use. According to one embodiment, a user places an oral treatment device that includes a wax-based barrier layer and an oral treatment composition into the user's mouth and then plastically deforms the wax-based barrier layer to better conform to the user's unique dentition in order to provide better fit and comfort. The oral treatment device can be self-customizable by the user as described herein, such as by warming the wax-based barrier layer to body temperature within the user's mouth and applying forces to plastically deform the barrier layer in order to at least partially customize the barrier layer so as to include indentations that conform to the user's unique dentition.

II. Wax-Based Compositions

Wax-based compositions as disclosed herein include a wax fraction, a polymer fraction homogeneously blended with the wax fraction, and optionally one or more auxiliary components. Examples of waxes that can be used include petroleum waxes, distilled waxes, synthetic waxes, mineral waxes, vegetable waxes, and animal waxes. Examples of polymers that can be used include synthetic and natural polymers. Examples of auxiliary components include plasticizers, flow modifiers, and fillers.

Examples of petroleum waxes include paraffin waxes (made of long-chain alkane hydrocarbons) (e.g., IGI 1260A), intermediate waxes (blend of long-chain and branched alkanes), microcrystalline waxes (branched alkane hydrocarbons of higher molecular weight and more amorphous than paraffin waxes) (e.g., IGI 5909A), distilled waxes (e.g., Astorstat® distilled waxes, such as Astorstat 6988, Astorstat 6920, 10069, Astorstat Astorstat 95, Astorstat 90, Astorstat 75, and Astorstat 10316), and petroleum jelly. Examples of synthetic waxes include polyethylene waxes (based on polyethylene), Fischer-Tropsch waxes (made from synthesis gas), chemically modified waxes (which are usually esterified or saponified), substituted amide waxes, and polymerized α-olefins. Examples of mineral waxes include ceresin waxes, montan wax (extracted from lignite and brown coal), ozocerite (found in lignite beds), and peat waxes. Examples of vegetable waxes include bayberry wax (from the surface wax of the fruits of the bayberry shrub, *Myrica faya*), candelilla wax (from the Mexican shrubs *Euphorbia cerifera* and *Euphorbia antisyphilitica*), carnauba wax (from the leaves of the Carnauba palm, *Copernica cerifera*), castor wax (catalytically hydrogenated castor oil), esparto wax (a byproduct of making paper from esparto grass, *Macrochloa tenacissima*), Japan wax (a vegetable triglyceride, from the berries of *Rhus* and *Toxicodendron* species), jojoba oil (pressed from the seeds of the jojoba bush, *Simmondsia chinensis*), ouricury wax (from the Brazilian feather palm, *Syagrus coronata*), rice bran wax (obtained from rice bran, *Oryza sativa*), and soy wax (from soybean oil). Examples of animal waxes include beeswax (produced by honey bees), Chinese wax (produced by the scale insect *Ceroplastes ceriferus*), lanolin (wool wax, from the sebaceous glands of sheep), and shellac wax (from the lac insect *Kerria lacca*).

Blends of waxes can be useful to incorporate materials properties from the different waxes. For example, paraffin wax, intermediate wax, and/or microcrystalline wax can be blended to provide a desired level of plastic deformation at room temperature and dimensional stability at higher temperatures. Paraffin, intermediate and microcrystalline waxes are all fully saturated hydrocarbon mixtures with the formula $C_nH_{2n+2}$. Paraffin waxes predominately include straight-chain alkanes, microcrystalline waxes predominately include branched alkanes of higher molecular weight than the alkanes in paraffin wax, and intermediate waxes have components and properties intermediate to those of paraffin and microcrystalline waxes. The effect of branching is to reduce melting point and increase viscosity. In general, paraffin waxes comprise mostly linear C18 to C40 alkanes, intermediate waxes have increased branching and comprise mostly C25 to C60 alkanes, and microcrystalline waxes contain little or no linear alkanes but rather complex, branched C25 to C85 alkanes.

As a general rule, the properties of paraffin wax and microcrystalline waxes can be generalized as follows:

| Paraffin Wax | Microcrystalline Wax |
| --- | --- |
| Low melting | Higher melting |
| White | Colored |
| Hard | Soft |
| Brittle | Malleable |
| Translucent | Opaque |
| Crystalline | Amorphous |
| Glossy | Adhesive |

The one or more waxes comprising the wax fraction of wax-based compositions as disclosed herein are typically included in an amount in a range of about 40% to about 95% by weight, preferably in a range of about 50% to about 93% by weight, more preferably in a range of about 60% to about 90% by weight, and most preferably in a range of about 70% to about 85% by weight of the wax-based composition.

The polymer fraction can include at least one type of polymer, examples of which include one or more polymers selected from polyolefins, polyesters, polyurethanes, thermoplastic elastomers, thermoset elastomers, and mixtures thereof. Examples of polyolefins include polyethylene (including high density polyethylene, HDPE), low density polyethylene, LDPE), or ultra-low density polyethylene, ULDPE), polypropylene (PP), and polytetrafluoroethylene (PTFE) (e.g., TEFLON), thermoplastic polyolefins (e.g., thermoplastic polyethylene, thermoplastic polypropylene, thermoplastic olefins), and propylene-based elastomers. Other synthetic polymers include ethylene-vinyl acetate copolymer (EVA), ethylene-vinyl alcohol copolymer (EVAL), polyvinyl acetate, polyvinyl alcohol, polyesters (such as polyethylene terephthalate, or PETE), polycarbonates, methacrylates, acrylates, polyamides (e.g., nylon), polyurethanes, polyvinyl chloride (PVC), synthetic rubber, phenol formaldehyde resin (Bakelite), neoprene, polystyrene, polyacrylonitrile, PVB, silicone elastomers, and thermoplastic elastomers (e.g., olefin-based elastomers, such as ethylene-, propylene- or butylene-based elastomers) (e.g., Engage™ thermoplastic elastomers, Vistamaxx™ thermoplastic elastomers, such as Vistamaxx™ 6102, Vistamaxx™ 6202, and Vistamaxx™ 3020, Duragrip® DGR 6250CL, and Thermolast® M TM6LFT). Natural polymeric materials include shellac, natural rubber, polysaccharides, cellulosic ethers, cellulose acetate, and proteins.

According to one embodiment, the polymer fraction can have high peroxide stability (i.e., so as to not cause decomposition of a peroxide bleaching agent) and/or good thermal stability (i.e., so as to yield a strip or tray that maintains its shape when exposed to elevated temperatures during shipping and storage).

The one or more polymers comprising the polymer fraction of wax-based compositions as disclosed herein are typically included in an amount in a range of about 5% to about 60% by weight, preferably in a range of about 7% to about 50% by weight, more preferably in a range of about 10% to about 40% by weight, and most preferably in a range of about 15% to about 30% by weight of the wax-based composition.

When included, the one or more auxiliary components (e.g., plasticizers, flow modifiers, and/or fillers) can be included in an amount in a range of about 0.01% to about 5% by weight of the wax-based composition, preferably in a range of about 0.1% to about 4% by weight, and more preferably in a range of about 1% to about 3% by weight of the wax-based composition.

At least a portion of the wax fraction, polymer fraction and/or auxiliary component can be similar to and/or provided by the materials contained in Parafilm®, which is sold in sheet form and which contains a proprietary blend of wax and polyolefin. Parafilm® M is a flexible sheet material with a paper backing to prevent self-adhesion and is commonly used to temporarily seal flasks or cuvettes in chemistry labs. Parafilm® F is commonly used in plant grafting. Parafilm® sheets typically soften at about 100° F. (or about 38° C.) and, if a Parafilm® sheet is thermoformed into a dental treatment tray, it begins to sag at temperatures of about 38° C. and above. As a result, oral treatment strips made using native Parafilm® as a barrier layer can become crinkled or shriveled at elevated temperatures during shipping and storage (i.e., which can reach 50° C. or more). Moreover, oral treatment strips made using native Parafilm® as the barrier layer can become excessively soft and gummy when placed in the mouth and exposed to body temperature over lengthy periods of time, permitting users to easily bite through and perforate the Parafilm® barrier layer, compromising its ability to function as a barrier to saliva.

Unexpectedly, however, when Parafilm® sheet material is cut into pieces and used as a feed material in an injection molding process, the resulting injection molded trays are thermally stable to a temperature above 40° C. (e.g., up to about 50-52° C. depending on the injection molding conditions). Therefore, the composition of "native" Parafilm® is apparently transformed into a new composition of matter when subject to temperatures and/or pressures associated with injection molding processes, such as those described herein. In addition, Parafilm® can be used as a blending component together with other components disclosed herein to yield trays or strips having thermal stability at temperatures of at least 40° C.

According to several embodiments, wax-based compositions are thermally stable (i.e., are dimensionally stable and resist significant deformation) when formed into a flat sheet or a three-dimensional article and heated to a temperature to which the sheet or article is typically subjected to during transport and storage. According to one embodiment, the wax-based composition is thermally stable when heated to a temperature of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70° C.

In addition, the wax-based composition can be plastically deformable. That is, the composition can be formed into a desired shape and then retain that shape absent application of an external force. According to one embodiment, the wax-based composition is plastically deformable and non-brittle at room temperature (25° C.). In other words, the wax-based composition can be configured into a desired shape without breaking or cracking and so as to retain that shape without heating to above room temperature. In other embodiments, the wax-based composition becomes plastically deformable at room temperature when extruded into a sheet or thermoformed or injection molded at elevated temperature into a desired three-dimensional article of a specified thickness. In some embodiments, the wax-based composition is semi-rigid at room temperature and becomes more flexible and deformable when heated to above room temperature, such as body temperature in the case of an oral treatment device that includes a wax-based barrier layer.

Depending on the relative concentrations of the wax and polymer fractions, the wax fraction may comprise a continuous phase and the polymer fraction may comprise a disperse phase within the continuous wax phase. Alternatively, the polymer fraction may comprise a continuous phase and the wax fraction may comprise a disperse phase within the continuous wax phase. In some cases, it is possible for the wax and polymer fractions to form an interpenetrating network without continuous and disperse phases.

An exemplary method of manufacturing a wax-based composition that is suitable for making sheets or articles that are thermally stable and plastically deformable includes: (1) combining a least one wax and at least one polymer to form a mixture; and (2) processing the mixture to form a wax-based composition that is comprised of a wax fraction homogeneously blended with a polymer fraction.

According to one embodiment, the at least one type of wax and the least one type of polymer are combined and processed using an extruder (e.g., a single screw or twin-screw extruder). The extruder can form the wax-based composition into the form of a sheet having a desired thickness. The sheet can be used as is or further shaped, such as by thermoforming, into a desired shape of an article of manufacture (e.g., a dental treatment tray). Alternatively, the extruder can form the wax-based composition into a strand that is cut into individual pellets, which can then be further processed, such as by injection molding, to form a desired shape of an article of manufacture. Other mixing apparatus known in the art can be used to form wax-polymer blends, which are then extruded, injection molded, or otherwise formed into a desired shape.

Example extruders can include a plurality of zones (e.g., 10 zones), such as mixing, heating and pressuring zones. The wax, polymer and auxiliary materials can be fed separately into the extruder in different zones or together in the same zone. For example, the one or more polymer components can be fed into zone 1, and the one or more wax components can be fed into zone 3. Auxiliary components, if used, can be fed into one of these zones or a different zone. The zones can have similar or different temperatures. In general, the materials fed into and mixed within the extruder can be subjected to one or more temperatures in a range of about 50° C. to about 225° C., preferably in a range of about 55° C. to about 210° C. More preferably the materials in the earlier zones are subjected to a higher temperature in a range of about 135° C. to about 220° C. and in the later zones to a lower temperature in a range of about 50° C. to about 125° C. in another part of the extruder, most preferably to a higher temperature in the earlier zones in a range of about 140° C. to about 210° C. and to a lower temperature in the later zones in a range of about 55° C. to about 120° C. The pressure within the extruder can be up to about 1000 psi, preferably up to about 100 psi, more preferably up to about 50 psi, and most preferably in a range of about 1 to about 25 psi.

Example injection molding apparatus include a hopper, a barrel with feeder screw, an injection nozzle, a valve gate, a mold cavity, and a mold core. In an injection molding process, the wax-based composition can be subjected to one or more initial temperatures for melting or softening the composition in a range of about 40° C. to about 200° C., preferably in a range of about 45° C. to about 150° C., and more preferably in a range of about 50° C. to about 120° C. The feeder barrel can have multiple heating zones of increasing temperature. In general, the highest temperature is reached at the valve gate. The softened or melted composition is introduced into the mold cavity under pressure in order to fill the mold cavity, such as at a pressure in a range of about 1000 psi to about 50,000 psi, preferably in a range of about 2500 psi to about 40,000 psi, more preferably in a range of about 5000 psi to about 30,000 psi, even more preferably in a range of about 7500 psi to about 20,000 psi, and most preferably in a range of about 10,000 psi to about 15,000 psi. To yield a solidified injection molded article, the mold core and cavity can have a reduced temperature in a range of about −10° C. to about 40° C., preferably in a range of about −5° C. to about 30° C., more preferably in a range of about 0° C. to about 25° C., even more preferably in a range of about 2° C. to about 20° C., and most preferably in a range of about 3° C. to about 10° C.

III. Articles Made from Wax-Based Compositions

Examples of articles that can be made from wax-based compositions as disclosed herein include, but are not limited to, sheets, oral treatment strips, sheets for sealing orifices, molded three-dimensional articles, and dental treatment trays. Sheet-like articles can be flat and are flexible and plastically deformable so as to be capable of being placed over an object and then wrapped around the object into a desired configuration that is able to maintain its shape. In some cases, the sheets can "customizable" in order to include 3-dimensional features of the object around which it is wrapped. Similarly, molded three-dimensional articles can be plastically deformable so as to be capable of being placed over an object and then further adapted to better fit over the object and better conform to the three-dimensional features of the object around over which it is adapted.

According to several embodiments, flat or curved sheets are provided that are plastically deformable at room temperature (25° C.) and thermally stable at temperatures of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70° C. (e.g., at temperatures between 50-75° C. depending on the formulation). This permits sheet-like articles made form the wax-based compositions disclosed herein to be manufactured, transported and stored at temperatures of 50-75° C. or more without losing their desired shape. The sheets comprise a wax-based composition that includes a wax fraction and a polymer fraction homogeneously blended with the wax fraction. The wax fraction includes at least one wax. The polymer fraction includes at least one polymer. The sheet can be formed by extruding the wax-based composition.

According to other embodiments, three-dimensional articles are provided that are plastically deformable at room temperature (25° C.) and thermally stable to temperatures of at least 40° C., or at least about 42.5° C., or at least about 45° C., or at least about 48° C., or at least about 50° C., or at least about 52.5° C., or at least about 55° C., or at least about 60° C., or at least about 65° C., or at least about 70° C. (e.g., at temperatures between 50-75° C. depending on the formulation) and are therefore dimensionally stable at elevated temperatures.

IV. Oral Treatment Devices and Kits

A. General Discussion

Disclosed herein are oral treatment devices that include a barrier layer comprised of a wax-based composition and an oral treatment composition disposed adjacent to and/or impregnated within the barrier layer. The barrier layer can be in the form of a tray or strip. A dental treatment tray typically includes at least one sidewall (e.g., at least a labial wall and optionally also a lingual wall) and a bottom wall adjacent to and extending laterally from the at least one sidewall (e.g., extending lingually from the labial wall or forming a transition or bridge between labial and lingual walls). Strip-like barriers and/or the at least one sidewall and bottom wall of a dental treatment tray comprise a wax-based composition that includes at least one wax and at least one polymer homogeneously blended with the wax. Oral treatment devices can be formed by thermoforming a wax-based sheet, injection molding a wax-based composition, or any other appropriate method known in the art.

According to several embodiments, oral treatment devices made from the wax-based compositions disclosed herein are plastically deformable at room temperature (25° C.) and thermally stable at temperatures of at least 40° C., or at least about 42.5° C., or at least about 45° C., or at least about 47.5° C., or at least about 50° C., or at least about 53° C., or at least about 55° C., or at least about 60° C., or at least about 65° C., or, or at least about 70° C. (e.g., at temperatures between 50-75° C. depending on the formulation) and are therefore dimensionally stable at elevated temperatures. This permits oral treatment devices made from the wax-based compositions disclosed herein to be manufactured, transported and stored at temperatures of 50-75° C. or more without losing their desired shape. Nevertheless, when placed into a user's mouth, dental treatment trays and strip-like barrier layers made from wax-based compositions disclosed herein can readily conform the size and shape of a user's unique dentition (e.g., are self-customizable in a user's mouth). They can readily conform to occlusal surfaces yet resisting perforation because they are not unduly softened at body temperatures.

According to one embodiment, the tray or strip can be non-customized and devoid of features corresponding to user's unique dentition. Once placed in a user's mouth, the tray or strip can warm to body temperature, which facilitates the ability of the tray or strip to at least partially conform to the user's unique dentition and thereby become at least partially customized. For example, the tray or strip can be at least partially customized in the user's mouth using shaping forces such as suctioning, biting and/or finger pressure. According to another embodiment, the tray can be customized (e.g., using a stone model of a user's teeth to register indentations in the tray corresponding to the user's unique dentition). Oral strips and trays are advantageously formulated so that it is difficult or impossible for a user to bite through the occlusal surface of the tray or strip in order to maintain a barrier to saliva.

Kits for providing oral treatments may include multiple oral treatment devices that include a wax-based barrier layer and one or more pre-applied oral treatment compositions. Alternatively, kits may include one or more wax-based barrier layers and one or more oral treatment compositions that can be applied to the barrier layers by the user at the time of use. Kits may include some barrier layers configured to fit over a person's upper teeth and other barrier layers configured to fit over a person's lower teeth.

Alternatively, a plurality of single-use, disposable customized dental treatment trays made from wax-based compositions as disclosed herein can be provided to a user in a kit. According to one embodiment, the kit of customized dental treatment trays permits the user to have the benefit of a new customized dental tray for every treatment event. Moreover, because of the plastically deformable nature of the wax-based composition, trays made therefore can be more comfortable and better fitting than professional custom-fitted trays.

A method of manufacturing a kit of single-use, disposable customized dental treatment trays includes: (1) taking an impression of a user's teeth using an impression material; (2) making a stone model of the user's teeth from the impression of the user's teeth; (3) providing a plurality of sheets comprised of a wax-based composition as disclosed herein; (4) thermoforming the sheets using the stone model to form the plurality of customized dental treatment trays; and (5) optionally trimming away excess tray material to maximize appropriate size and fit. The single-use, disposable customized wax-based dental treatment trays can be used in a kit that includes an oral treatment composition that is loaded into the trays by the user or they can be pre-loaded with an oral treatment composition.

Regardless of its form, the barrier layer is typically moisture-resistant in order to protect the oral treatment composition from saliva in a user's mouth. Because waxes and polymers tend to be hydrophobic, wax-based compositions as disclosed herein will typically be moisture-resistant. The wax-based barrier layers will typically have a thickness in a range of about 0.025 mm to about 1.5 mm, or from about 0.05 mm to about 1.25 mm, or from about 0.075 mm to about 1 mm, or from about 0.09 mm to about 0.75 mm, or from about 0.1 mm to about 0.5 mm, or from about 0.15 mm to about 0.35 mm.

According to one embodiment, the occlusal walls of example dental treatment trays can have a greater cross-sectional thickness than the one or more sidewalls (e.g., between about 20-100% thicker, or about 30-75% thicker, or about 40-60% thicker). This provides several benefits, including the ability of the dental treatment trays to be self-customized to a user's teeth without the user biting through and perforating the occlusal wall. It can also increase dimensional stability of the dental treatment trays by providing a more rigid base to which the one or more sidewalls are attached without compromising comfort and fit. The occlusal wall is typically the last wall to contact a user's teeth during installation such that increased rigidity of the occlusal wall does not significantly decrease the ability of the thinner sidewall(s) to be customized or adapted to the user's labial and/or lingual tooth surfaces. Moreover, because the occlusal wall can be easily self-customized to the user's occlusal tooth surfaces by biting, the user can readily self-customize the occlusal wall regardless of increased thickness. And in fact, increased thickness is most beneficial in the occlusal region, which is subjected to the greatest customization forces (i.e., biting).

Another benefit of providing a thickened occlusal wall is that it facilitates injection molding of relatively thin-walled dental treatment trays from the wax-based compositions disclosed herein. Because the occlusal wall of a molded tray is typically approximately midway between the labial and lingual walls, the mold cavity in the region corresponding to a thickened occlusal wall will be wider than adjacent regions corresponding to the thinner labial and lingual walls. A wider mold cavity in the middle region of the mold facilitates injection molding by providing better flow of the softened wax-based composition throughout the mold cavity.

Oral treatment compositions can include at least one active agent, at least one tissue adhesion (or thickening) agent, a liquid or gel solvent, carrier or vehicle into which the active agent and tissue adhesion agent are dispersed, and other components and adjuvants as desired. The treatment composition may comprise continuous or discontinuous beads or layers positioned so as to contact at least a portion of a person's tooth surfaces and/or gums. Treatment compositions can have a consistency of a liquid, gel, sticky viscous material, putty, or solid. Solids and putties can become more sticky and adhesive to teeth and/or gums when moistened with water or saliva. In some cases, the main difference between a "gel" and a "putty" or "solid" is the level of solvent or carrier within the composition. In general, the greater the concentration of solvent or carrier relative to the tissue adhesive agent, the less viscous is the composition. The lower the concentration of solvent or carrier relative to the tissue adhesion agent, the more viscous, putty-like or solid is the composition.

Examples of active agents for oral treatment compositions include dental bleaching agents, desensitizing agents, remineralizing agents, antimicrobial agents, anti-plaque agents, anti-tartar agents, gingival soothing agents, anesthetics, antioxidants, and mouth freshening agents. Examples of dental bleaching agents include aqueous hydrogen peroxide, carbamide peroxide, metal perborates (e.g., sodium perborate), metal percarbonates (e.g., sodium percarbonate), metal peroxides (e.g., calcium peroxide), metal chlorites and hypochlorites, peroxy acids (e.g., peroxyacetic acid), and peroxy acid salts.

Bleaching agents within dental bleaching compositions according to the invention can have any desired concentration, e.g., between 1-90% by weight of the dental bleaching composition. The concentration of the dental bleaching agent can be adjusted depending on the intended treatment time for each bleaching session. The bleaching agent is preferably included in an amount in a range of about 1% to about 60% by weight, more preferably in a range of about 3% to about 40% by weight, and most preferably in a range of about 5% to about 30% by weight. When a dental bleaching agent is used, the materials used to make the wax-based composition can be selected so as to not prematurely react with and destabilize the bleaching agent.

Examples of desensitizing agents include potassium nitrate, other potassium salts, citric acid, citrates, and sodium fluoride. Examples of remineralizing agents in sodium fluoride, stannous fluoride, sodium monofluorophosphate, and other fluoride salts. Examples of antimicrobial agents and preservatives include chlorhexidine, triclosan, sodium benzoate, parabens, tetracycline, phenols, cetyl pyridinium chloride, and benzalkonium chloride. An example of an anti-plaque or anti-tartar agent is pyrophosphate salts. Examples of gingival soothing agents include aloe vera, mild potassium nitrate, and isotonic solution-forming salts. Examples of anesthetics include benzocaine and lidocaine. Examples of antioxidants include vitamin A, vitamin C, vitamin E, other vitamins, and carotene. Examples of mouth freshening agents include camphor, oil of wintergreen, peppermint, spearmint, and methyl salicylate.

Tissue adhesion agents, tackifying agents, or thickening agents can include a wide variety of hydrophilic polymers. Examples include polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethyl-cellulose, carboxypropylcellulose, cellulosic ethers, polysaccharide gums, proteins, and the like. Examples of PVPs include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

In the case where the oral treatment composition is a gel, the one or more tissue adhesion agents are preferably included in an amount in a range of about 1% to about 50% by weight of the treatment gel, more preferably in a range of about 3% to about 30% by weight, and most preferably in a range of about 5% to about 20% by weight.

In the case where the oral treatment composition is a putty or solid, the one or more tissue adhesion agents are preferably included in an amount in a range of about 10% to about 90% by weight of the substantially solid treatment composition, more preferably in a range of about 20% to about 80% by weight, and most preferably in a range of about 40% to about 75% by weight.

Liquids and gels, including sticky viscous gels, may include one or more liquid or gel, solvents, carriers or vehicles into which the active agent, tissue adhesion agent, and other components are dissolved or dispersed. Examples of liquid or gel solvents, carriers or vehicles include water, alcohols (e.g., ethyl alcohol), and polyols (e.g., glycerin, sorbitol, mannitol, other sugar alcohols, propylene glycol, 1,3-propanediol, polyethylene glycol, polyethylene oxide, and polypropylene glycol).

For solids or stiff putties, the concentration of solvent, carrier or vehicle will typically be attenuated compared to treatment gels. Where it is desired to convert a gel into a putty or solid composition, it may be advantageous to include one or more volatile solvents that can be removed by evaporation (e.g., water, alcohols, acetone, and other organic solvents). Because of the affinity of hydrophilic polymers for water, even treatment compositions that appear to be solid may include a significant amount of bound water (e.g., up to about 10% or more by weight of the treatment composition). In the case where the treatment composition has the consistency of a highly viscous or stiff putty, the composition will generally include a solvent, carrier or vehicle that acts as a plasticizer or softening agent.

Oral treatment compositions may optionally include other components as desired to yield treatment compositions having desired properties. Examples include bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal polyphosphates, and alkyl sulfates), neutralizing agents (e.g., sodium hydroxide and triethanolamine), inorganic thickening agents (e.g., fumed silica), colorants, flavorants, sweeteners, and the like.

According to one embodiment, oral treatment devices can have a horseshoe-shaped longitudinal profile and a trough with a U-shaped cross section, as in conventional bleaching trays. Alternatively, oral treatment devices can have barrier layers with other shapes, such as flat strips that are rectangular or contoured to fold around and fit over a user's teeth.

Other examples of articles made from wax-based compositions as disclosed herein include, but are not limited to, therapeutic delivery devices (e.g., trays or strips) used to deliver therapeutic agents day or night to geriatric patients, convalescent patients, patients with poor hygiene, intubated humans, or other patients to treat a variety of conditions, including dry mouth, infections, dental conditions, tooth sensitivity, and the like. Examples of active oral agents include, but are not limited to, fluoride, desensitizing agents, anesthetics, remineralizing agents, anti-plaque agents, anti-tartar agents, antimicrobial agents, antibiotics, chlorhexidine, doxycycline, or healing agents for soft oral tissues). The active oral agents can be contained within compositions of varying rheology, including but not limited to, sticky viscous compositions, substantially solid compositions, putty-like compositions, less viscous or fluid compositions. By way of example, a fluoride treatment composition can be a sticky viscous gel or, alternatively, may be a less viscous, more fluid composition that can be easily rinsed from a patient's teeth. Alternatively, a solid active agent (e.g., doxycycline or other antibiotic for treating periodontal pockets) can be embedded in a wall of a wax-based tray or strip and held against or near a region of oral tissue for prolonged treatment.

Therapeutic devices may include a barrier liner made from a wax-based composition and an oral treatment composition pre-loaded therein (e.g., a sticky, viscous composition, substantially solid composition, or putty-like material). Alternatively, therapeutic devices may include a barrier liner made from a wax-based composition and an absorbent insert or lining (e.g., absorbent paper or sponge material) that acts as a reservoir to retain more fluid, less viscous oral compositions within the tray and adjacent to teeth and/or oral tissues that might otherwise diffuse or be expressed from the device into the oral cavity in an undesired manner.

Other treatment devices include, but are not limited to, orthodontic guard devices (e.g., a tray or strip) to protect soft oral tissues from orthodontic devices that might cause irritation, particularly when first installed, including orthodontic guard trays and strips that can form a barrier between irritating features of an orthodontic device and soft oral tissues; devices for treating disorders of the temporomandibular joint ("TMJ") ("TMJ disorders" or "TMD"); anti-bruxing devices; customizable sports mouth guards, including customizable inserts for sports mouth guards and two-color molded sports mouth guards; deformable strips or sheets for registering occlusal points; and surgical trays designed to protect oral tissues after oral surgeries and/or deliver therapeutic agents.

B. Example Illustrations

Figure 1B:
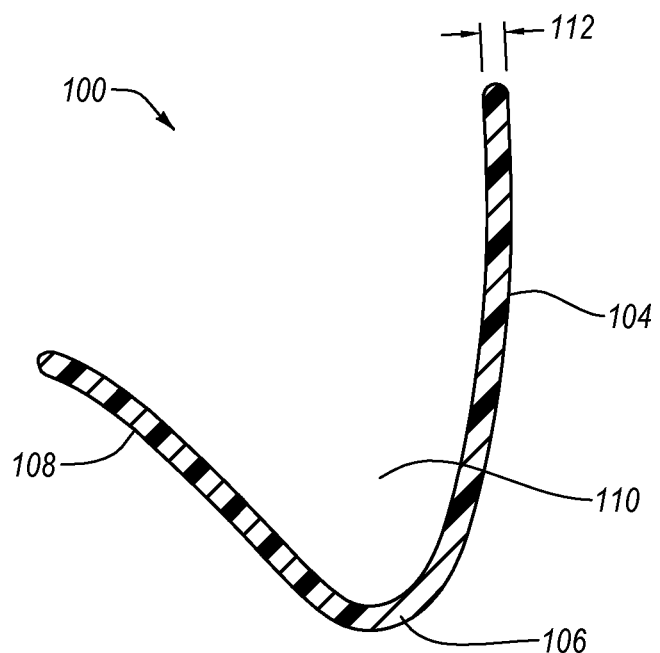

Reference is now made to the drawings, which illustrate several embodiments of oral treatment devices as disclosed herein. FIGS. 1A and 1B illustrate an oral treatment tray or insert 100 fashioned from a wax-based material as disclosed herein. Tray or insert 100 generally includes a flexible, three-dimensional body 102 having a generally horseshoe shaped configuration defined by a labial wall 104, an occlusal wall 106 extending laterally (e.g., lingually) from labial wall 104, and a lingual wall 108 extending laterally (e.g., occlusally-gingivally) from occlusal wall 106. Labial wall 104, occlusal wall 106, and lingual wall 108 together define a trough 110 having a generally U-shaped cross section.

FIG. 1B is a cross-section view of the tray or insert 100 of FIG. 1A taken along line 1B-1B. As illustrated in this view, labial wall 104, occlusal wall 106, and lingual wall 108 provide body 102 with a substantially continuous wall thickness 112. It will be appreciated, however, that tray or insert 100 may have variable thicknesses in different regions to provide desired functionality.

Oral treatment tray or insert 100 can be used to provide a variety of different functions and may have different and/or varying thicknesses depending on its intended use. When used as a treatment tray to deliver a medicament or other active oral agent, tray 100 can be thin-walled, flexible, and readily adaptable to a person's teeth in order to provide good fit and comfort. Because the wax-based composition of tray 100 is plastically deformable, the tray body 102 is able to register and maintain the unique shape and size of a person's unique dentition. When used as an oral treatment tray to deliver an oral agent, labial wall 104, lingual wall 106, and occlusal wall 108 can have the same or different thicknesses in a range of about 0.001" to about 0.04", or about 0.002" to about 0.02", or about 0.004" to about 0.01", or about 0.005" to about 0.008".

In the case where oral treatment device 100 is used for a purpose other than merely delivering a medicament or other oral care composition, such as protecting soft oral tissues from irritation, body 102 can have a cross-sectional thickness that is thicker, at least in some reasons, and potentially softer and more flexible. For example, where a patient has been fitted with orthodontic devices or recently had oral surgery (e.g., and has wires or rods in the mouth), the tray should be sufficiently thick, yet flexible to register, ameliorate and cushion sharp points or protrusions that might otherwise irritate soft oral issues when contacted therewith. The soft wax-based tray 100 is able to provide a smoother and more uniform surface that is gentle on soft oral tissues. The tray 100 may also either have a unique shape to accommodate a particular type of hardware or appliance within a person's mouth and/or it may be highly adaptable in order to readily conform to the hardware or appliance.

In the case where oral treatment device 100 is used to treat TMJ disorders, tray body 102 can have an occlusal wall 108 that has sufficient cross-sectional thickness and firmness to provide a desired therapeutic effect. For example, it may be desirable to keep the molars from coming together. In such case, the posterior portion of occlusal wall 108 can have a thickness and firmness to provide the desired bridging and/or levering effect to relieve pain in the TMJ and promote healing. The exact thickness may vary on a case-by-case basis and can be prescribed by a dentist or oral surgeon. In general, the thickness of TMJ trays as disclosed herein can be in a range of about 0.01" to about 0.2", preferably in a range of about 0.025" to about 0.15", and more preferably in a range of about 0.05" to about 0.1".

In the case where oral treatment device 100 is used as an anti-bruxing device, tray body 102 can have an occlusal wall 108 that has sufficient cross-sectional thickness and firmness to provide a desired therapeutic effect. For example, it may be desirable to keep the molars and other teeth from grinding together at night during sleep. In such case, the posterior portion of occlusal wall 108 can have a thickness and firmness to provide the desired anti-bruxing effect to protect the teeth. The exact thickness may vary on a case-by-case basis and can be prescribed by a dentist. In general, the thickness of anti-bruxing trays as disclosed herein can be in a range of about 0.001" to about 0.1", preferably in a range of about 0.005" to about 0.08", and more preferably in a range of about 0.01" to about 0.05".

Oral treatment device 100 can also be used as a sports mouth guard or as a self-customizable insert for a molded polymer mouth guard shell with a trough designed to accommodate a customizable insert made of a wax-based material. In the case where oral treatment device 100 provides the sports mouth guard structure, the tray body 102 can have a thickness in a range of about 3 mm (about ⅛") to about 6 mm (about ¼") in order to protect teeth from sharp blows or impacts during sporting events. The tray body 102 may be formed by two-color molding, with a flexible, yet firm and durable outer mouth guard shell, which is able to receive and distribute impact forces that can occur during sporting events and which can be made from any suitable polymer material, and an inner customizable layer made of a wax-based composition as disclosed herein that is capable of being customized by the user to register the user's unique dentition and maximize fit and comfort. In such cases, the mouth guard shell can have a thickness in a range of about 0.1" to about 0.3", preferably in a range of about 0.12" to about 0.275", and more preferably in a range of about 0.14" to about 0.2" and the inner customizable layer made of a wax-based composition can have a thickness in a range of about 0.005" to about 0.15", preferably in a range of about 0.02" to about 0.125", and more preferably in a range of about 0.02" to about 0.1".

When tray body 102 is a customizable insert for a sports mouth guard, it can have a thickness in a range of about 0.005" to about 0.15", preferably in a range of about 0.02" to about 0.125", and more preferably in a range of about 0.02" to about 0.1". In some cases, tray body 102 can be a disposable insert that is used for a single or multiple sporting events, removed and then replaced by a new tray body 102 for a future sporting event. In this way, the tray body 102 can be easily customized and then replaced in the event it becomes deformed or stretched over time during one or more sporting events.

While the following drawings are discussed in terms of being dental treatment trays for use in delivering a dental treatment composition, it should be understood that any may be modified to function for any desired use, including the various devices and uses described above with reference to FIGS. 1A and 1B and other parts of the disclosure.

Figure 1C:
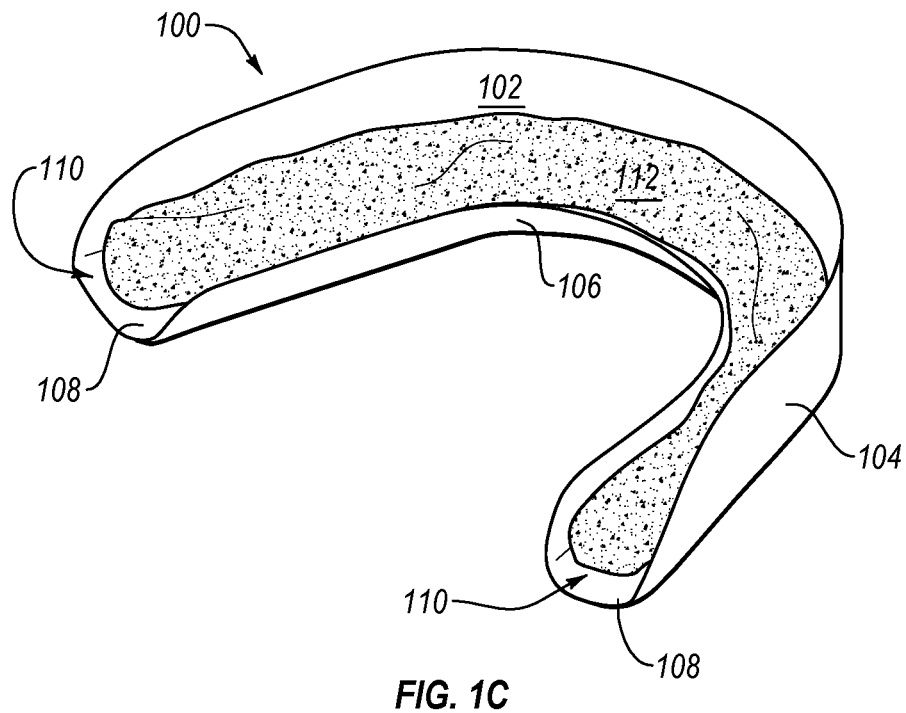
FIGS. 1C-1D illustrate exemplary oral treatment devices that include a dental treatment tray and a gel or solid oral treatment composition within the tray.

FIG. 1C is a perspective view of an oral treatment device 100 comprising a wax-based barrier layer 102 having a front side wall 104, a rear side wall 106, and a horseshoe shaped bottom wall 108 that together define a trough 110 having a generally U-shaped cross section throughout the horseshoe. Disposed within trough 110 is a an oral treatment composition 112 that can be a gel, such as a sticky, viscous gel, which can assist in reliably holding the dental treatment tray in proper position over a user's teeth during use. Oral treatment composition 112 may have a consistency ranging from a gel, a sticky viscous gel, to a solid treatment composition. Oral treatment composition 112 can be a viscous gel having a cross-sectional diameter or thickness in a range of about 1 mm to about 5 mm, more preferably in a range of about 2 mm to about 4 mm. The gel can be a continuous bead of composition.

Figure 1D:
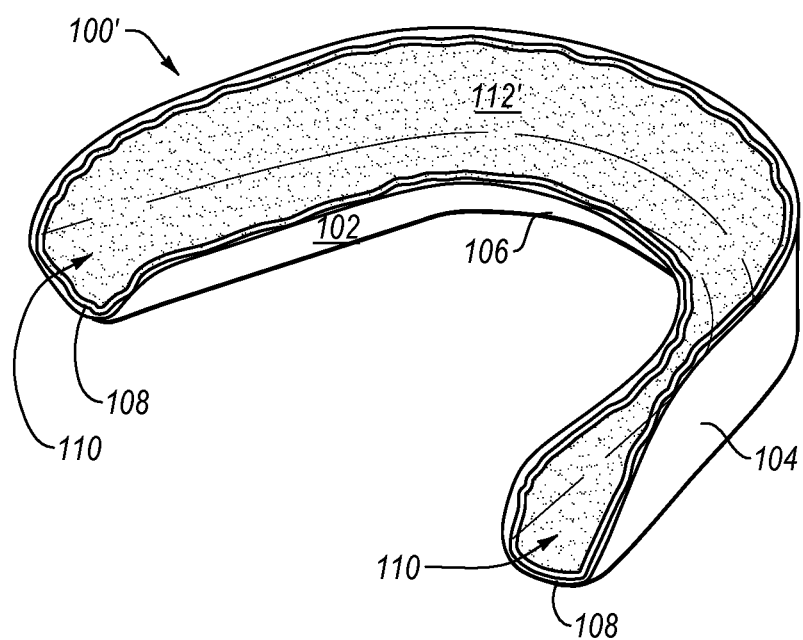

FIG. 1D depicts an oral treatment device 100' that includes a wax-based barrier layer 102 in the form of a dental tray having a horseshoe shape with a substantially U-shaped cross section. Barrier layer 102 includes front sidewall 104, rear sidewall 106, and bottom wall 108 that together define a trough 110 having a general U-shaped cross section. Within trough 110 is an oral treatment composition 112' that substantially covers the interior walls rather than being a bead of composition. Oral treatment composition 112' may be a gel, a sticky viscous gel, a putty, or a solid composition. Treatment composition 112' is preferably a stiff putty or solid having a thickness in a range of about 0.2 mm to about 2 mm, more preferably in a range of about 0.5 mm to about 1 mm.

In an alternative embodiment, FIG. 1D may be understood as illustrating an oral treatment device 100' that includes a wax-based barrier layer 102 in the form of a dental tray having a horseshoe shape with a substantially U-shaped cross section, as described above, and an absorbent liner 112' positioned inside of trough 110 for retaining an oral treatment composition within trough 110 and against teeth (not shown) during use. Absorbent liner 112' may comprise any known absorbent material, examples of which include absorbent paper, open cell foam, and the like. Absorbent liner 112' can be used, for example, when the oral treatment composition is sufficiently fluid or of low viscosity as to easily run out of the trough 110 or be easily squeezed out of trough 110 as a result of mild pressure applied to the wax-based barrier layer. In the case where oral treatment device 100' is used to provide therapeutic agents to invalids and remain in the mouth for long periods of time (e.g., 4 hours or more), the absorbent liner 112' helps maintain prolonged contact between the oral treatment composition and the teeth and/or gums.

Figure 2A:
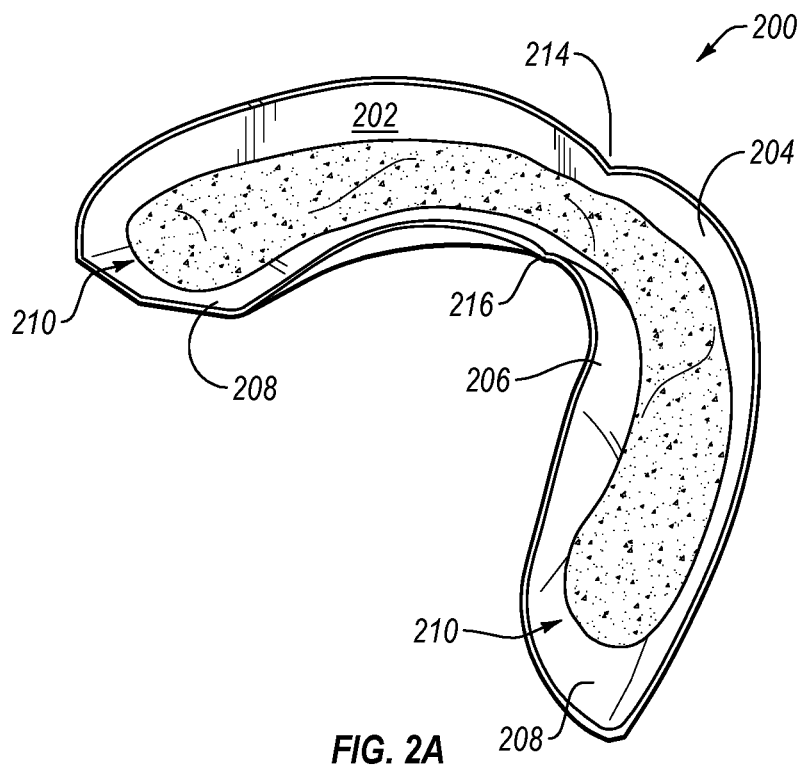
FIGS. 2A-2B illustrate exemplary oral treatment devices that include a dental treatment tray having features that assist the treatment device in conforming to the shape of a user's dental arch and a gel or solid oral treatment composition within the tray.
Figure 2B:
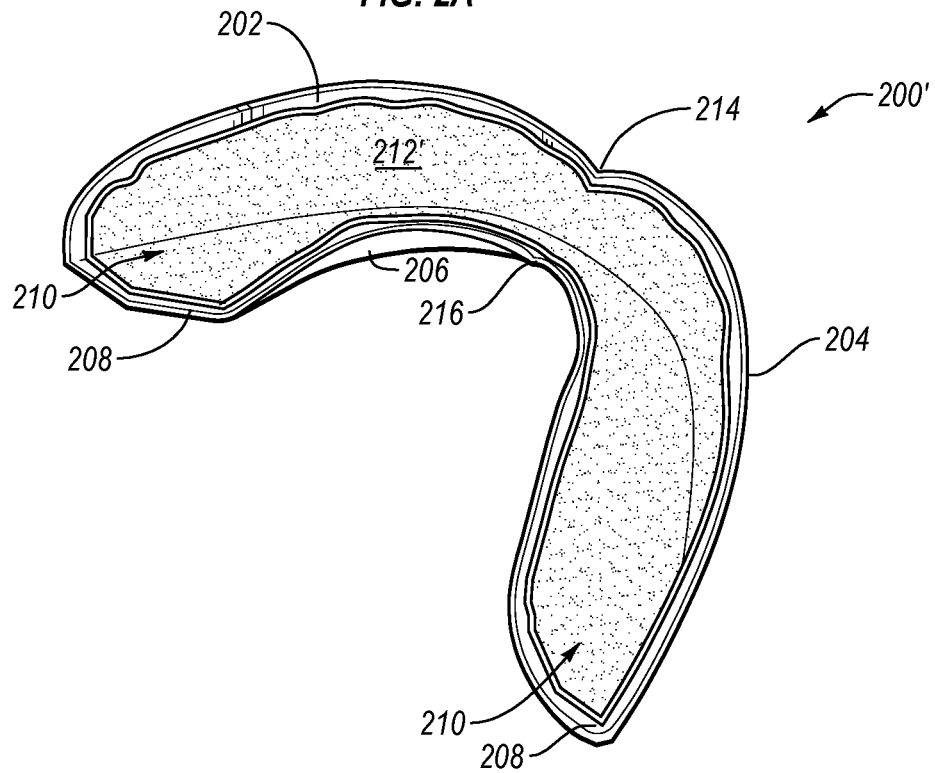

FIGS. 2A and 2B depict oral treatment devices 200, 200', each of which include a barrier layer 202 having a front sidewall 204, a rear sidewall 206, and a bottom wall 208 that together define a trough 210 into which either a bead of treatment composition 212 (FIG. 2A) or a continuous layer of treatment composition 212' (FIG. 2B) is disposed. In addition, oral treatment devices 200, 200' include a first notch 214 in front sidewall 204 and a second notch 216 in rear sidewall 206. Notches 214 and 216 assist the oral treatment devices 200, 200' in conforming to variously sized and shaped dental arches.

Figure 3A:
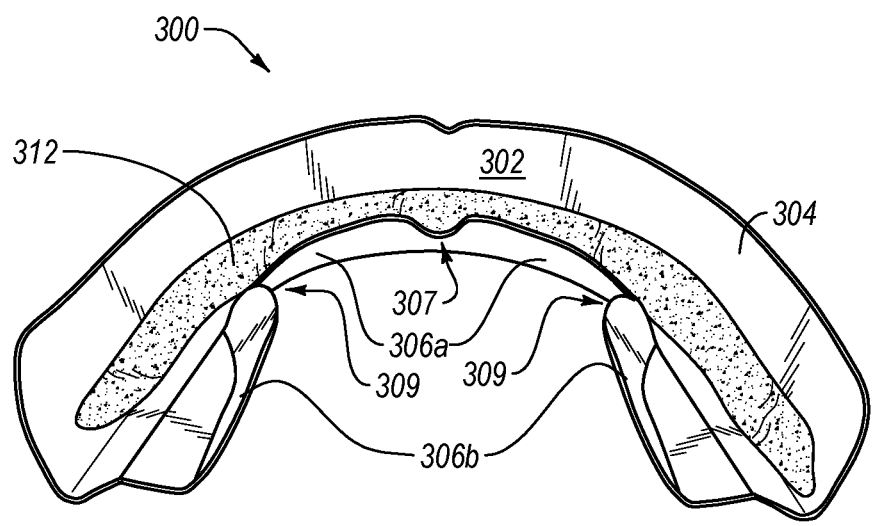
FIGS. 3A-3B illustrate exemplary oral treatment devices that include a dental treatment tray with cuts or discontinuities that assist the treatment device in conforming to the shape of a user's dental arch and a gel or solid oral treatment composition within the tray
Figure 3B:
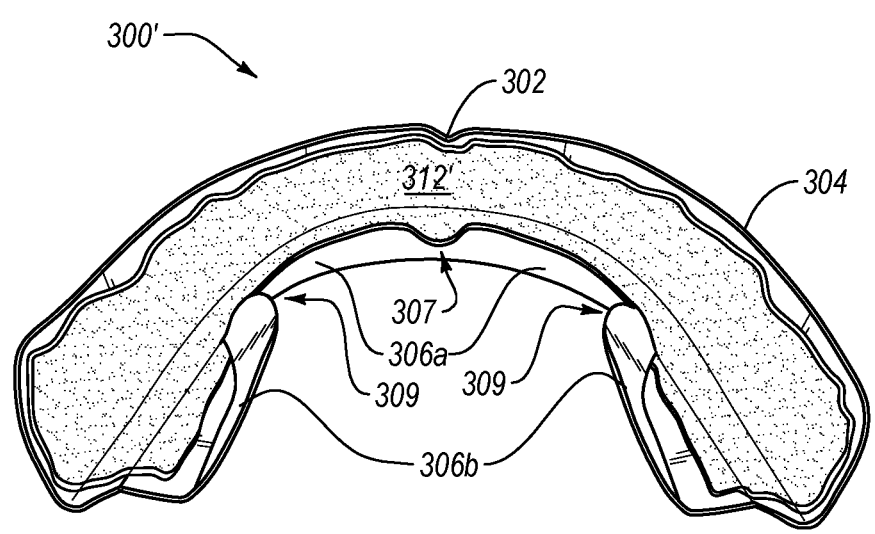

FIGS. 3A and 3B depict oral treatment devices 300, 300' with features that assist the barrier layers in better conforming to the size and shape of variously dental arches. Instead of continuous sidewalls, oral treatment devices 300, 300' includes a barrier layer 302 having a front sidewall 304, a rear sidewall 306, and a bottom wall 308 interconnecting front sidewall 304 and rear sidewall 306. Rear sidewall 306 further includes a first rear sidewall section 306a that includes a first cut or discontinuity 307 and a second rear sidewall section 306b separated from first rear sidewall section 306a by second cuts or discontinuities 309. The first rear sidewall section 306a is configured to wrap around and lie adjacent to inner surfaces of a person's incisors and canines. Second rear sidewall section 306b is configured to wrap around and contact inner surfaces of a person's bicuspids and optionally one or more molars.

Cuts or discontinuities 309 between first and second sidewall sections 306a, 306b facilitate good fit against a person's incisors and canines, particularly at the junction of the canines and bicuspids. Cuts or discontinuities 309 compensate for the abrupt difference in width between a person's bicuspids adjacent to the second rear sidewall section 306b and the canines adjacent to the first rear sidewall section 306a. Discontinuity or cut 307 in first sidewall section 306a further assists in conforming first sidewall section 306a to inner surfaces of a person's incisors and canines.

FIG. 3A further shows a continuous bead of an oral treatment composition 312 within an interior region or trough defined by front sidewall 304, rear sidewall 306, and bottom wall 308. FIG. 3B alternatively depicts a substantially continuous layer of an oral treatment composition 312' disposed within an interior region or trough defined by front sidewall 304, rear sidewall 306, and bottom wall 308.

Figure 4A:
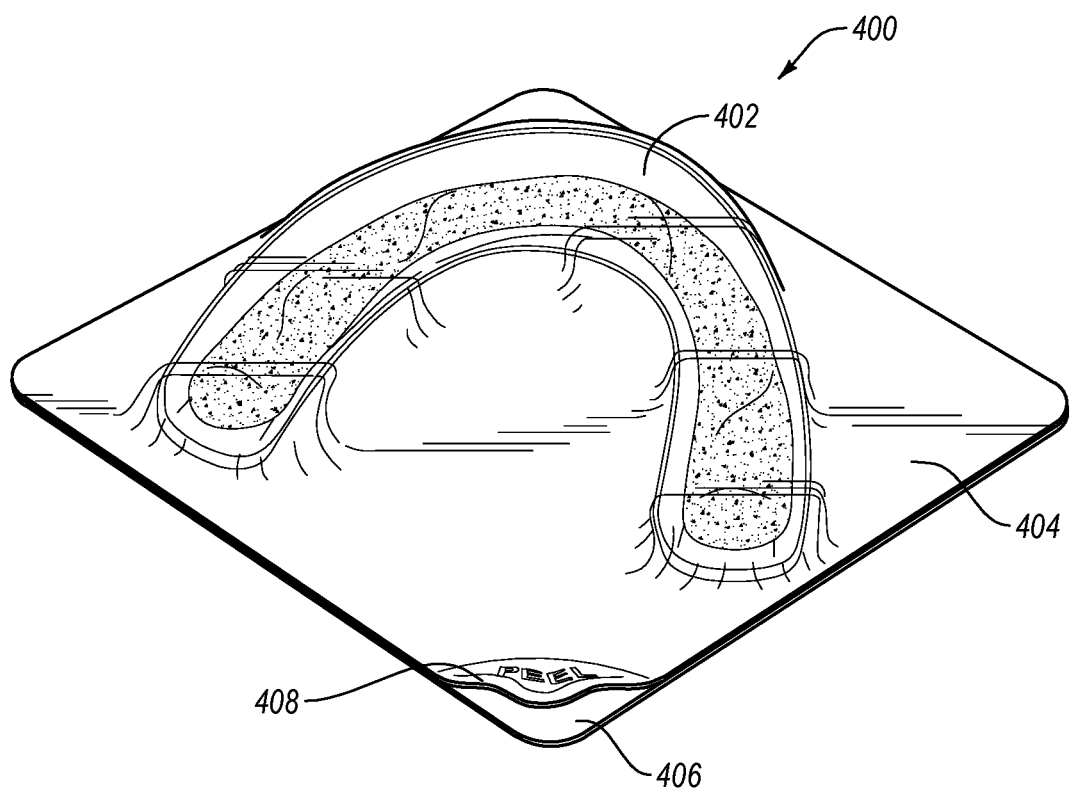
FIGS. 4A-4B illustrate oral treatment devices contained within sealed protective packages having a peelable cover.
Figure 4B:
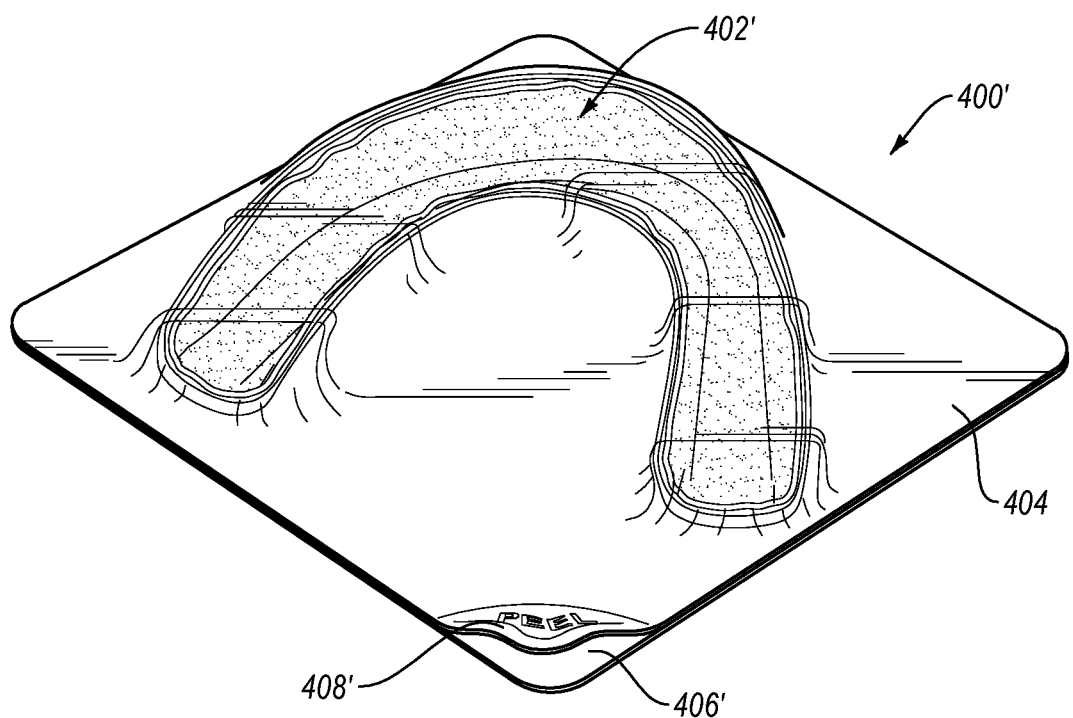

To protect oral treatment devices from contaminants during storage and prior to use, treatment devices can be packaged within a sealed container or package. As illustrated in FIGS. 4A and 4B, exemplary sealed oral treatment packages 400, 400' include an oral treatment device 402, 402' (e.g., dental treatment trays) sealed within a protective package 404, 404'. Protective packages 404, 404' includes a rigid support layer 406, 406' and a peelable cover 408, 408'. When it is desired to use oral treatment device 402, 402', the peelable cover 408, 408' is removed and treatment device 402, 402' is removed or separated from support layer 406, 406'.

FIGS. 5A and 5B depict an embodiment of an oral treatment device in the form of a treatment strip rather than a treatment tray. Oral treatment strip 500 includes a strip of wax-based material 502, which is initially substantially flat and can optionally have rounded corners. Strip of wax-based material 502 may be a single layer of wax-based material comprised of a homogeneous blend of wax and polymer. Coated onto and/or impregnated into strip of wax-based material 502 is an oral treatment composition 504. Oral treatment composition 504 can be a homogeneous material, uniformly and continuously coated onto strip of wax-based material 502.

FIGS. 6A and 6B illustrate an oral treatment device 600 applied to and closely conforming to a surface of a tooth 602. Oral treatment device 600 may include a barrier layer in the form of a dental treatment tray or strip-like sheet that is wrapped around tooth 602 to form a tray-like configuration. Oral treatment device 600 also includes an oral treatment composition that is able to provide a desired treatment to teeth and/or gums. While oral treatment device 600 is shown so that it only covers tooth 602 and not adjacent soft oral tissue 604, it is within the scope of the disclosure for the oral treatment device 600 to extend beyond gingival margin 606 and at least partially overlap soft oral tissue 604.

Figure 7A:
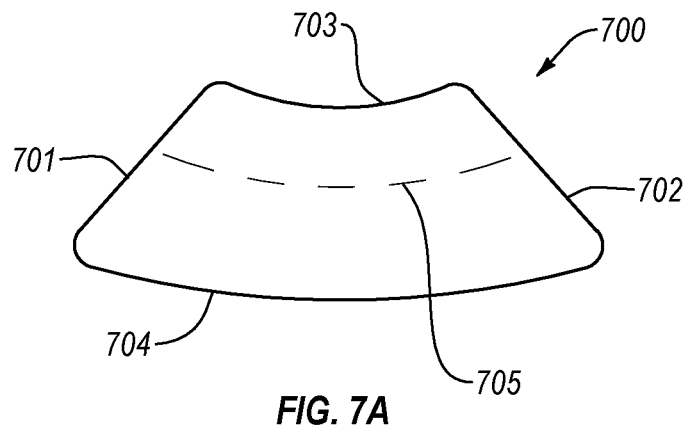
FIGS. 7A-7E illustrate various shapes of strip-like barrier layers that can be used in fashioning oral treatment devices according to the invention.

FIGS. 7A-7E illustrate various embodiments of strip-like barrier layers, which can be placed over a user's teeth and/or gums and adapted so as to wrap around and contact both labial and lingual surfaces. FIG. 7A illustrates an embodiment of a strip of wax-based material 700 that is substantially trapezoidal in shape. Strip 700 has a first side 701, a second side 702, a third side 703, and a fourth side 704. First side 7011 and second side 702 are generally straight sides that angle inward from fourth side 704 toward third side 703. Third side 703 can be concave and shorter then fourth side 704, while fourth side 704 can be convex. In use, fourth side 704 can be placed adjacent to the gingival margin at an intersection between a user's teeth and gums. A fold line 705 may be included in strip 700, which extends from first side 701 to second side 702. Fold line 705 may be located closer to third side 703 or fourth side 704 depending on the desired size and shape of the device when folded during use. Fold line 705 may be determined by the size of a user's teeth and the manner of placement of the oral treatment strip on the user's teeth. Third side 703 will be positioned adjacent to the lingual surfaces of the user's teeth upon folding strip 700 along fold line 705.

Figure 7B:
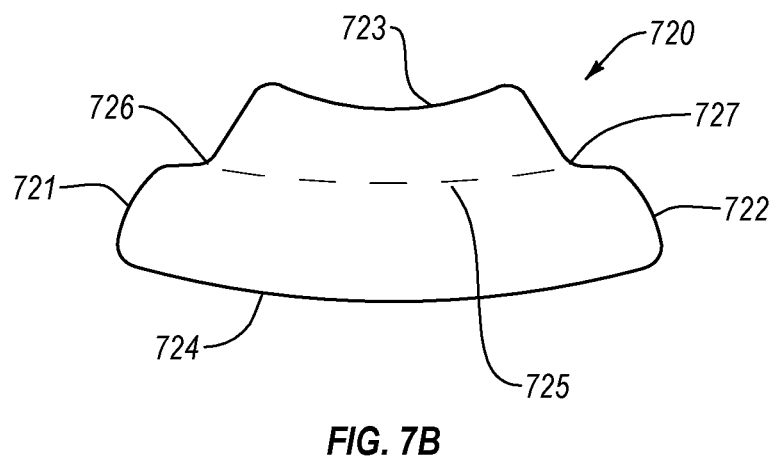

FIG. 7B illustrates another embodiment of a strip of wax-based material 720 that is substantially trapezoidal in shape with stair-stepped sides. Strip 720 has a first side 721, a second side 722, a third side 723, and a fourth side 724. Third side 723 can be concave and shorter then fourth side 724. Fourth side 724 can be convex. First side 721 and second side 722 are both stair step sides that include inner corners 726, 727, respectively. A fold line 725 typically extends between inner corners 726, 727 of the stair steps in first side 721 and second side 722, respectively.

Figure 7C:
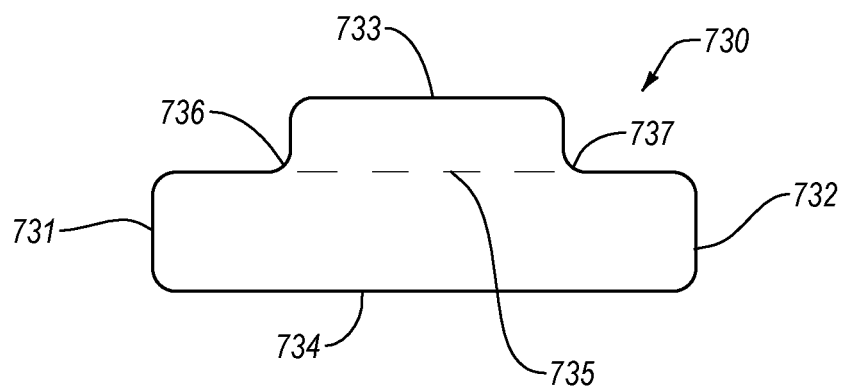

FIG. 7C illustrates an alternative embodiment of a strip of wax-based material 730 that is substantially rectangular in shape with stair-stepped sides. Strip 730 includes a first side 731, a second side 732, a third side 733, and a fourth side 734. First side 731 and second side 732 are both stair step sides that include inner corners 726, 727, respectively. A fold line 735 extends from the corners 736 and 737 of the stair steps in first side 731 and second side 732, respectively. Fold line 35 can be placed over occlusal surfaces of a user's teeth, which permits the strip 700 to fold around and over both the labial and lingual surfaces of the user's teeth. Strip 700 can be placed so that the user's two canine teeth are just outside of corners 736 and 737. Fourth side 734 can be located close to the gingival margin of the front side of a user's teeth. Third side 733 will be located along the lingual surface of the user's teeth.

Figure 7D:
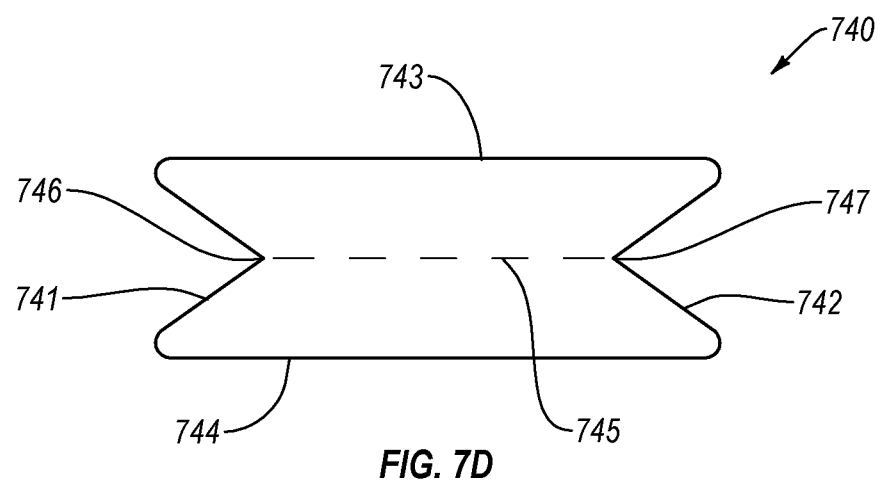

FIG. 7D illustrates an alternative embodiment of a strip of wax-based material 740 that is substantially rectangular in shape but with notched sides. Strip 740 has a first side 741, a second side 742, a third side 743, and a fourth side 744. Third side 743 and fourth side 744 are both substantially straight sides and can be the same length. First side 741 and second side 742 include notches 746, 747, respectively, which enable the occlusal surfaces of a user's canine teeth to not be covered when the strip 740 is placed over the user's teeth. A fold line 745 can extends from notch 746 in first side 741 to notch 747 in second side 742. Notches 746, 747 can have sideways V shapes as shown. However, the notches can be of any desired shape, including rectangular, square, semicircular, oval, and the like and that allow the tips of the canine teeth to not be covered by strip 740 when worn over the user's teeth.

Figure 7E:
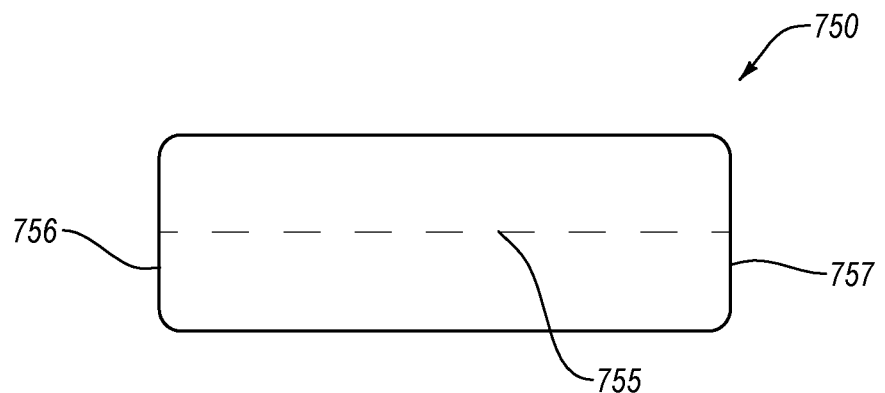

FIG. 7E illustrates an alternative embodiment of a strip of wax-based material 750 that is substantially rectangular in shape but with a fold line 755 between sides 756 and 757 in order to facilitate folding around occlusal edges of a user's teeth during installation. Once installed over a person's teeth, strip or sheet 750 can maintain an oral treatment composition against or near oral tissue to be treated.

Figure 8A:
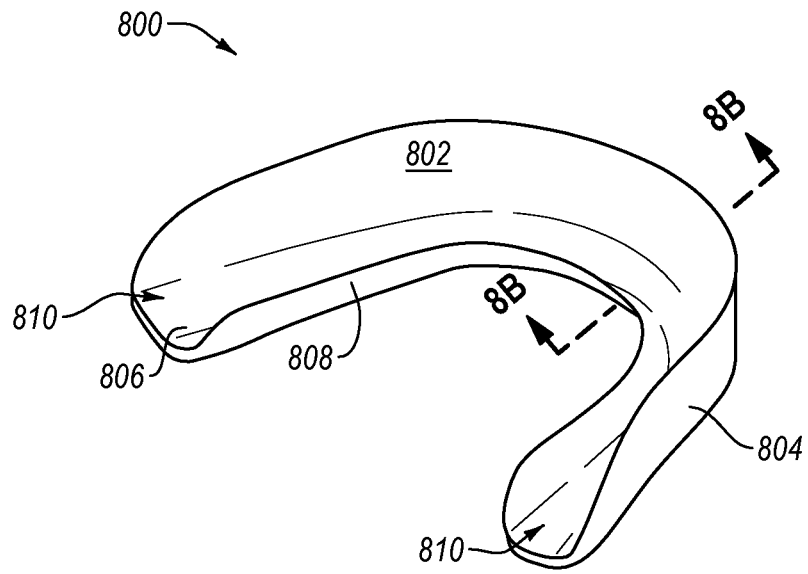
FIG. 8A is a perspective view illustrating an exemplary oral treatment device having a barrier layer with a thickened occlusal wall and thinner labial and lingual walls.
Figure 8B:
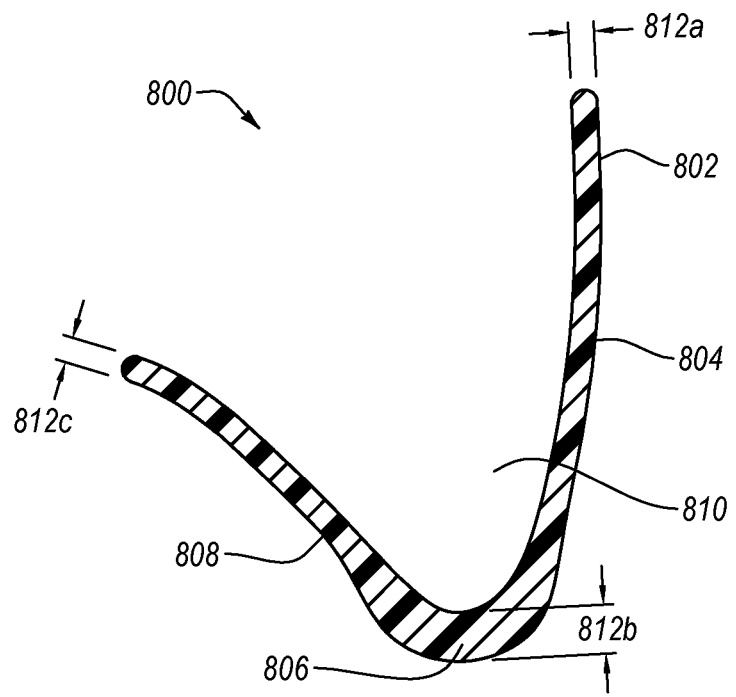
FIG. 8B is a cross-section view of the treatment device of FIG. 8A taken along line 8B-8B schematically illustrating the thickened occlusal wall compared to the thinner labial and lingual walls.

The flat strip or sheet 750 illustrated in FIG. 7E can be used for purposes other than to deliver oral treatment agents. For example, the strip or sheet 750 was be used to register occlusal points during a dental examination procedure. Strip or sheet 750 can be made from a deformable wax-based material that can permanently deform and register occlusal points, which permits a dental practitioner to fashion a dental restoration in a proper fashion in order for the restored tooth to properly contact and function together with a corresponding tooth during chewing FIGS. 8A and 8B illustrate an exemplary oral treatment device or tray having a thickened occlusal wall and thinner labial and lingual walls. A thickened occlusal wall can provide several benefits, including providing additional wax-based material in regions that are likely to be deformed the most during self-customization and/or require increased thickness to provide a desired function.

FIG. 8A is a perspective view of an oral treatment device 800 comprising a barrier layer 802 having a generally horseshoe shaped configuration defined by a labial wall 804, an occlusal wall 806 extending laterally (e.g., lingually) from labial wall 804, and a lingual wall 808 extending laterally (e.g., occlusally-gingivally) from occlusal wall 806. Labial wall 804, occlusal wall 806, and lingual wall 808 together define a trough 810 having a generally U-shaped cross section.

FIG. 8B is a cross-section view of oral treatment device 800 of FIG. 8A taken along line 8B-8B that schematically illustrates the relative cross-sectional thicknesses 818 of labial wall 804, occlusal wall 806, and lingual wall 808. Labial wall 804 has a labial wall thickness 812a, occlusal wall 806 has an occlusal wall thickness 812b, and lingual wall 808 has a lingual wall thickness 812c. For delivering oral treatment compositions, labial wall thickness 812a and/or lingual wall thickness 812c can be in a range of about 0.001" to about 0.01", about 0.002" to about 0.008", or about 0.004" to about 0.007". Occlusal wall thickness 812b can be in a range of about 0.002" to about 0.04", about 0.005" to about 0.025", or about 0.008" to about 0.015" and be at least about 25%, 30%, 40%, 50%, 75% or 100% greater than the labial and/or lingual wall thickness 812a, 812c.

In the case where the oral treatment device 800 is used for other purposes (e.g., as a TMJ device, anti-bruxing device, sports mouth guard, sports mouth guard liner, orthodontic guard tray, or surgical tray), the various wall thicknesses can be adjusted for the specific purpose for which the oral treatment device 800 is designed.

When oral treatment device 800 is used as a TMJ tray, at least occlusal wall 806 can have a thickness in a range of about 0.01" to about 0.2", preferably in a range of about 0.025" to about 0.15", and more preferably in a range of about 0.05" to about 0.1".

When oral treatment device 800 is used as an anti-bruxing tray, at least occlusal wall 806 can have a thickness in a range of about 0.001" to about 0.1", preferably in a range of about 0.005" to about 0.08", and more preferably in a range of about 0.01" to about 0.05".

When oral treatment device 800 is used as a sports mouth guard, at least occlusal wall 806 can have a thickness in a range of about 3 mm (about ⅛") to about 6 mm (about ¼") in order to protect teeth from sharp blows or impacts during sporting events. Barrier layer 802 may be formed by two-color molding, with a flexible, yet firm and durable outer mouth guard shell, which is able to receive and distribute impact forces that can occur during sporting events and which can be made from any suitable polymer material, and an inner customizable layer made of a wax-based composition as disclosed herein that is capable of being customized by the user to register the user's unique dentition and maximize fit and comfort. In such cases, at least the outer shell portion of occlusal wall 806 can have a thickness in a range of about 0.1" to about 0.3", preferably in a range of about 0.12" to about 0.275", and more preferably in a range of about 0.14" to about 0.2" and the inner customizable layer made of a wax-based composition can have a thickness in a range of about 0.005" to about 0.15", preferably in a range of about 0.02" to about 0.125", and more preferably in a range of about 0.02" to about 0.1".

When oral treatment device 800 is used as a customizable insert for a sports mouth guard, at least occlusal wall 806 can have a thickness in a range of about 0.005" to about 0.15", preferably in a range of about 0.02" to about 0.125", and more preferably in a range of about 0.02" to about 0.1".

Figure 8C:
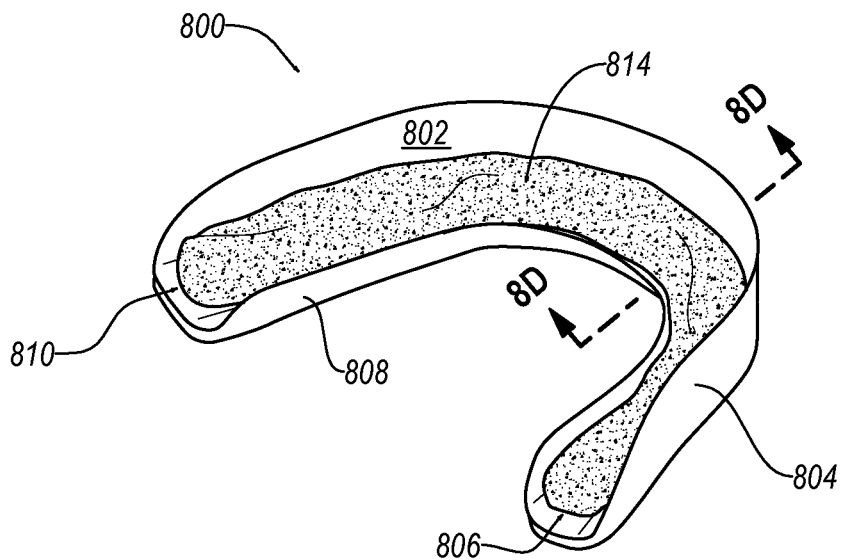
FIG. 8C is a perspective view illustrating an exemplary pre-filled oral treatment device having a barrier layer with a thickened occlusal wall, thinner labial and lingual walls, and an oral treatment composition positioned on a lingual side of the barrier layer.
Figure 8D:
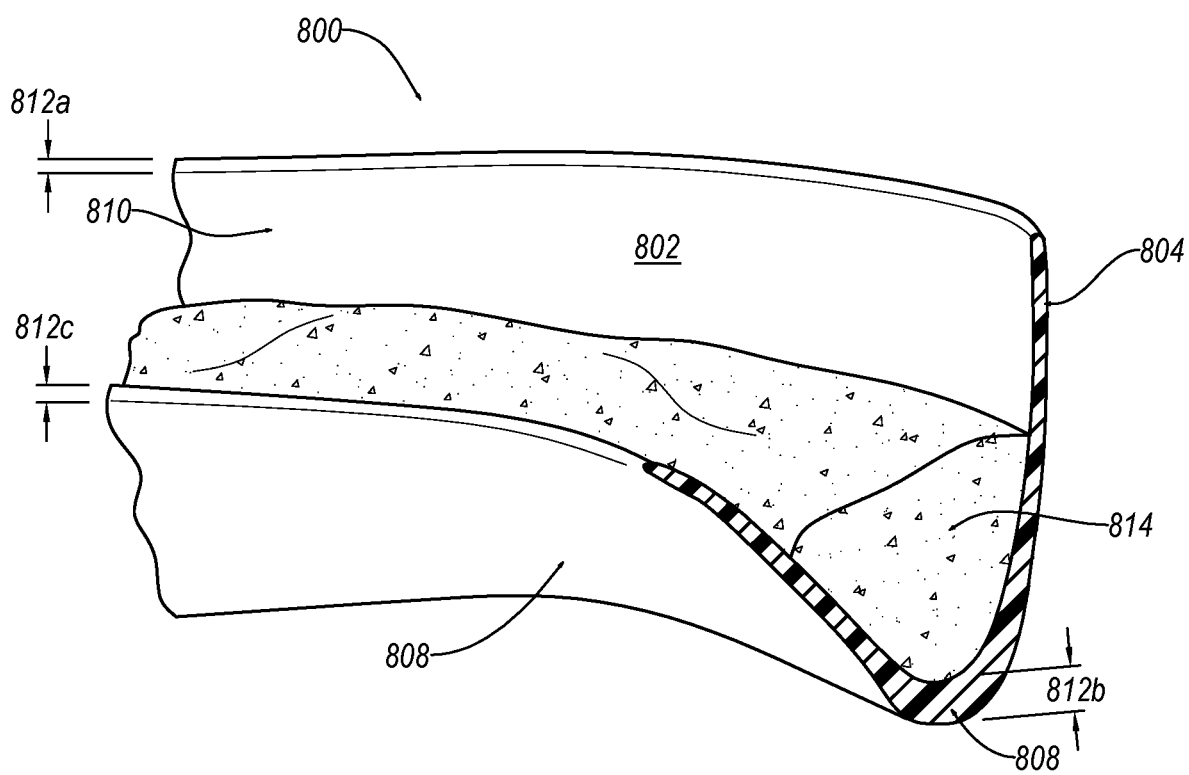
FIG. 8D is a cross-section view of the pre-filled oral treatment device of FIG. 8C taken along line 8D-8D schematically illustrating the thickened occlusal wall compared to the thinner labial and lingual walls and the treatment composition.

FIGS. 8C and 8D illustrate an exemplary pre-filled oral treatment device or tray with a barrier layer having a thickened occlusal wall and thinner labial and lingual walls. FIG. 8C is a perspective view of pre-filled oral treatment device 800 including a flexible barrier layer 802 having a generally horseshoe shaped configuration defined by a labial wall 804, an occlusal wall 806 extending laterally (e.g., lingually) from labial wall 804, and a lingual wall 808 extending laterally (e.g., occlusally-gingivally) from occlusal wall 806. Labial wall 804, occlusal wall 806, and lingual wall 808 together define a trough 810 having a generally U-shaped cross section and that holds oral treatment composition 814 therein. According to one embodiment, oral treatment composition 814 can be a bead of gel or viscous putty.

FIG. 8D is a cross-section view of pre-filled oral treatment device 800 of FIG. 8C taken along line 8D-8D that schematically illustrates the relative cross-sectional thicknesses 812 of labial wall 804, occlusal wall 806, and lingual wall 808. Labial wall 804 has a labial wall thickness 812*a*, occlusal wall 806 has an occlusal wall thickness 812*b*, and lingual wall 808 has a lingual wall thickness 812*c*. Labial wall thickness 812*a*, occlusal wall thickness 812*b*, and lingual wall thickness 812*c* can be as described herein.

Figure 9A:
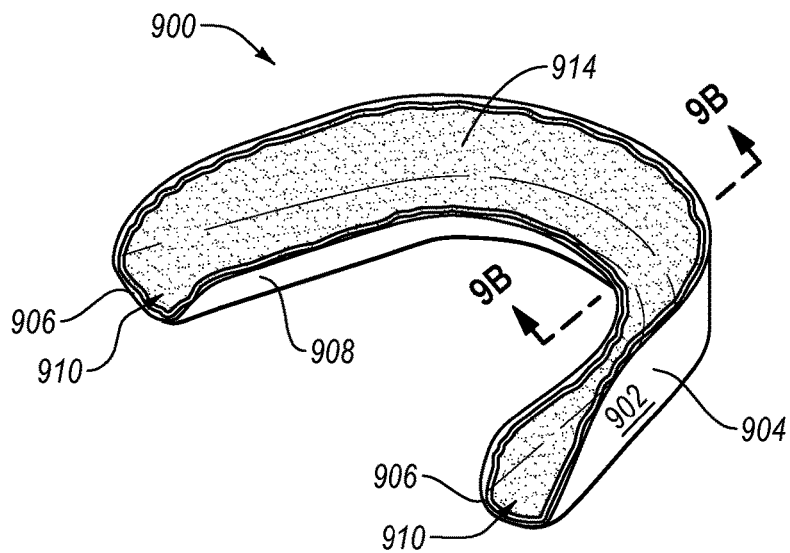
FIG. 9B is a cross-section view of the pre-filled oral treatment device of FIG. 9A taken along line 9B-9B schematically illustrating the thickened occlusal wall compared to the thinner labial and lingual walls and the substantially solid treatment composition.
Figure 9B:
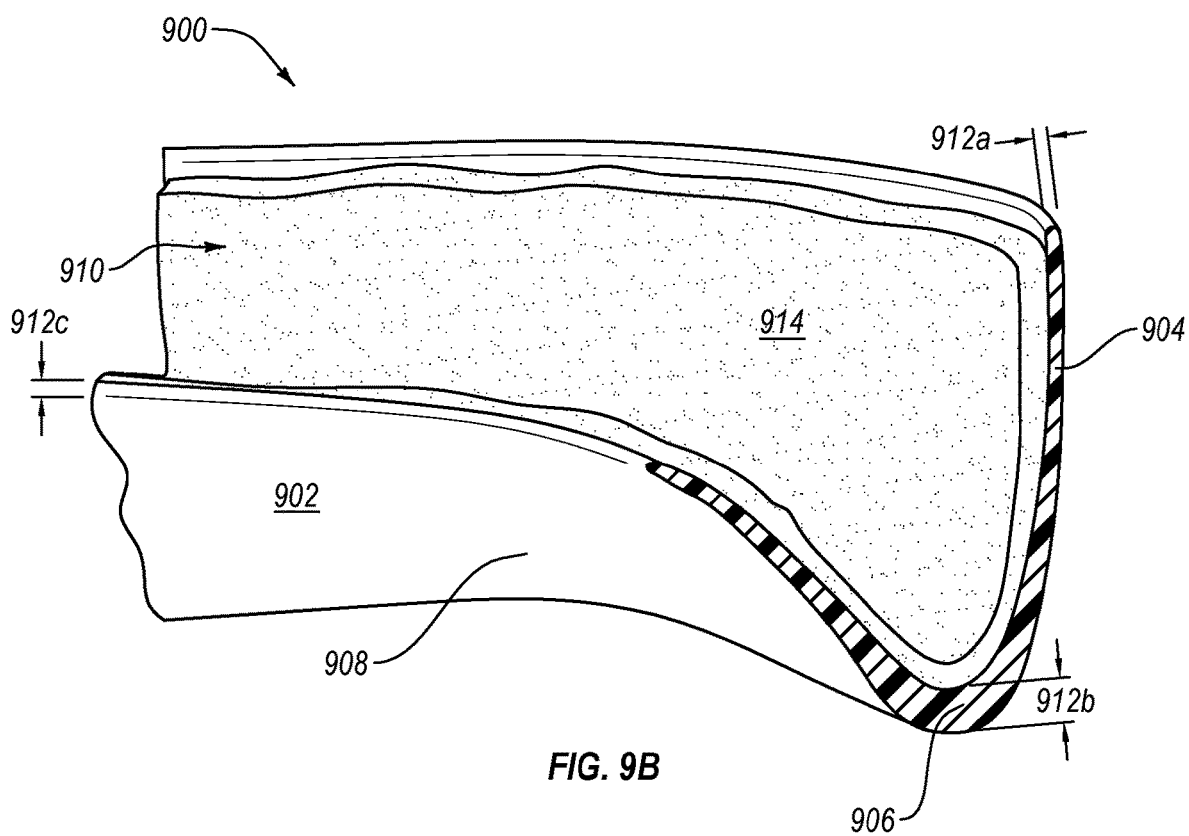

FIGS. 9A and 9B illustrate an exemplary pre-filled oral treatment device or tray with a barrier layer having a thickened occlusal wall and thinner labial and lingual walls. FIG. 9A is a perspective view of pre-filled oral treatment device 900 including a flexible barrier layer 902 having a generally horseshoe shaped configuration defined by a labial wall 904, an occlusal wall 906 extending laterally (e.g., lingually) from labial wall 904, and a lingual wall 908 extending laterally (e.g., occlusally-gingivally) from occlusal wall 906. Labial wall 904, occlusal wall 906, and lingual wall 908 together define a trough 910 having a generally U-shaped cross section and that holds oral treatment composition 914 therein. According to one embodiment, oral treatment composition 914 can be substantially solid and/or initially dry to the touch but become more adhesive to teeth and/or gums when moistened with saliva or water.

FIG. 9B is a cross-section view of pre-filled oral treatment device 900 of FIG. 9A taken along line 9B-9B that schematically illustrates the relative cross-sectional thicknesses 912 of labial wall 904, occlusal wall 906, and lingual wall 908. Labial wall 904 has a labial wall thickness 912*a*, occlusal wall 906 has an occlusal wall thickness 912*b*, and lingual wall 908 has a lingual wall thickness 912*c*. Labial wall thickness 912*a*, occlusal wall thickness 912*b*, and lingual wall thickness 912*c* can be as described herein.

In an alternative embodiment, oral treatment device 900 may alternatively include an absorbent liner 914, which holds therein a more fluid and less viscous oral composition.

Figure 10A:
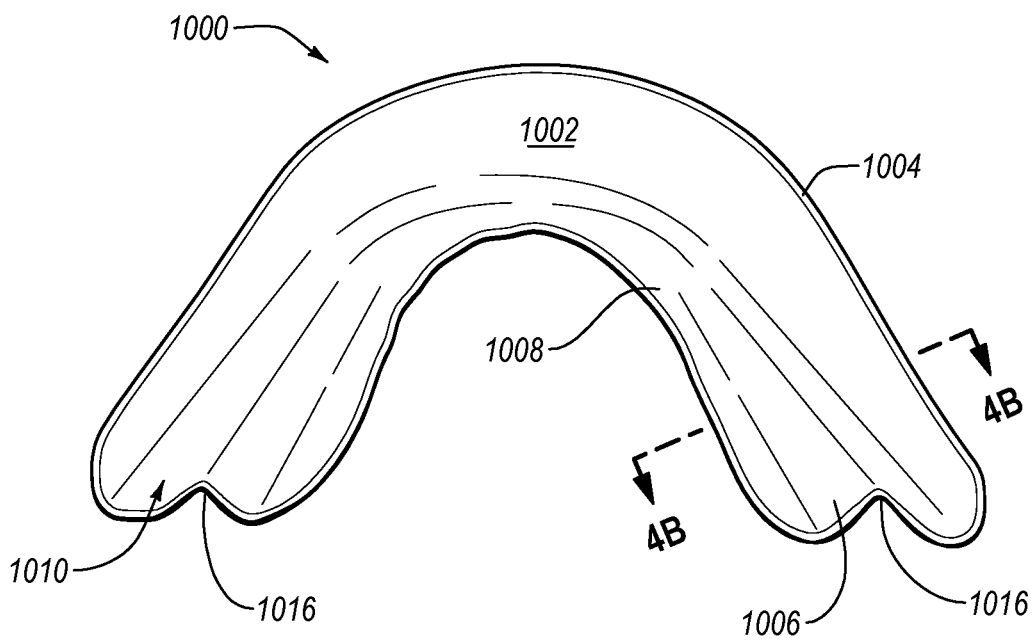
FIG. 10A is a perspective view illustrating an exemplary oral treatment device having a thickened occlusal wall compared to the labial and lingual walls and a non-customized V-shaped protrusion in the occlusal wall configured to fit into depressions in adjacent posterior teeth and improve fit between the oral treatment device and a person's dental arch when worn.
Figure 10B:
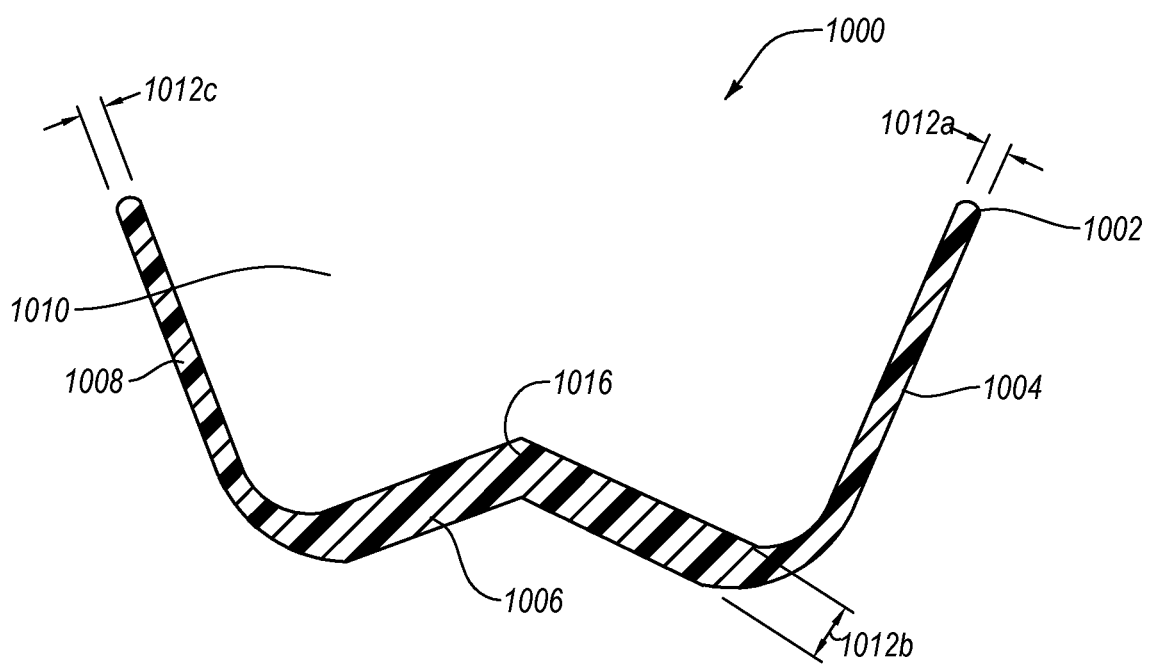
FIG. 10B is a cross-section view of the oral treatment device of FIG. 10A taken along line 10B-10B schematically illustrating the thickened occlusal wall compared to the thinner labial and lingual walls and the V-shaped protrusion.

FIGS. 10A and 10B illustrate an exemplary oral treatment device or tray having a thickened occlusal wall with a V-shaped protrusion and thinner labial and lingual walls. FIG. 10A is a perspective view of an oral treatment device 1000 comprising a flexible barrier layer 1002 having a generally horseshoe shaped configuration defined by a labial wall 1004, an occlusal wall 1006 extending laterally (e.g., lingually) from labial wall 1004, and a lingual wall 1008 extending laterally (e.g., occlusally-gingivally) from occlusal wall 1006. Labial wall 1004, occlusal wall 1006, and lingual wall 1008 together define a trough 1010 for receiving an oral treatment composition. Trough is further defined by a non-customized V-shaped protrusion 1016 formed in occlusal wall 1006, which is included in order to enhance fit between occlusal wall 1006 and indentations naturally found in posterior teeth (i.e., bicuspids and molars). This, in turn, results in less overall deformation of occlusal wall 1006 when customized to fit against a person's unique dentition.

FIG. 10B is a cross-section view of oral treatment device 1000 of FIG. 10A taken along line 10B-10B that schematically illustrates the relative cross-sectional thicknesses 1012 of labial wall 1004, occlusal wall 1006, and lingual wall 1008 as well as V-shaped protrusion 1016 formed by occlusal wall 1006. Labial wall 1004 has a labial wall thickness 1012*a*, occlusal wall 1006 has an occlusal wall thickness 1012*b*, and lingual wall 1008 has a lingual wall thickness 1012*c*. Labial wall thickness 1012*a* and/or lingual wall thickness 1012*c* can be in a range of about 0.001" to about 0.01", about 0.002" to about 0.008", or about 0.004" to about 0.007". Occlusal wall thickness 1012*b* can be in a range of about 0.002" to about 0.04", about 0.005" to about 0.025", or about 0.008" to about 0.015" and be at least about 25%, 30%, 40%, 50%, 75% or 100% greater than the labial and/or lingual wall thickness 1012*a*, 1012*c*.

In the case where the oral treatment device 1000 is used for other purposes (e.g., as a TMJ device, anti-bruxing device, sports mouth guard, sports mouth guard liner, orthodontic guard tray, or surgical tray), the various wall thicknesses can be adjusted for the specific purpose for which the oral treatment device 1000 is designed.

Figure 11A:
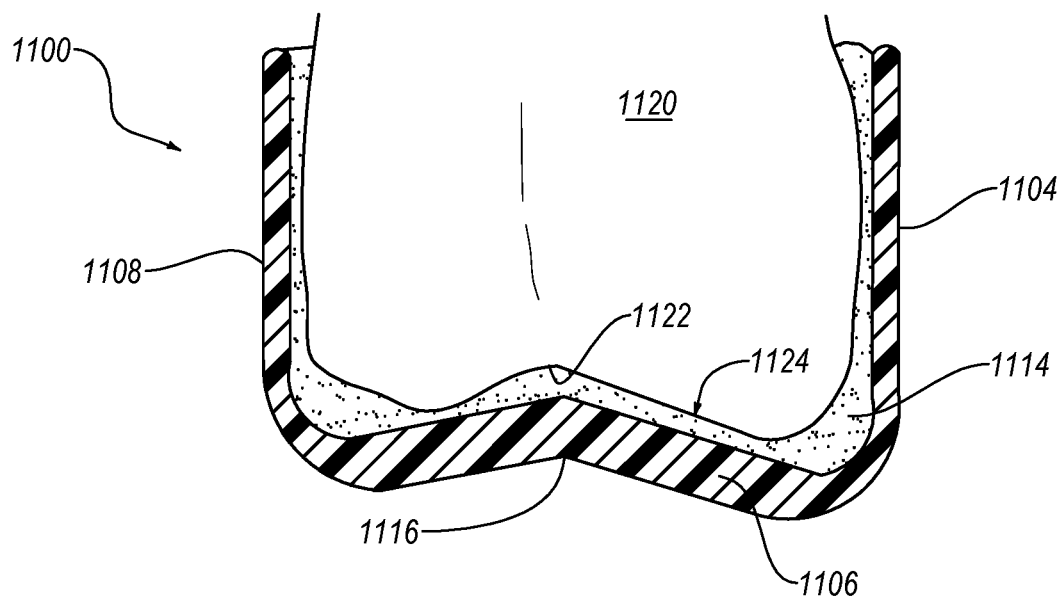
FIG. 11A illustrates an exemplary oral treatment device in use in maintaining an oral treatment composition against a posterior tooth, the treatment device having a thickened occlusial wall and V-shaped protrusion to enhance fit within a recess of the posterior tooth.
Figure 11B:
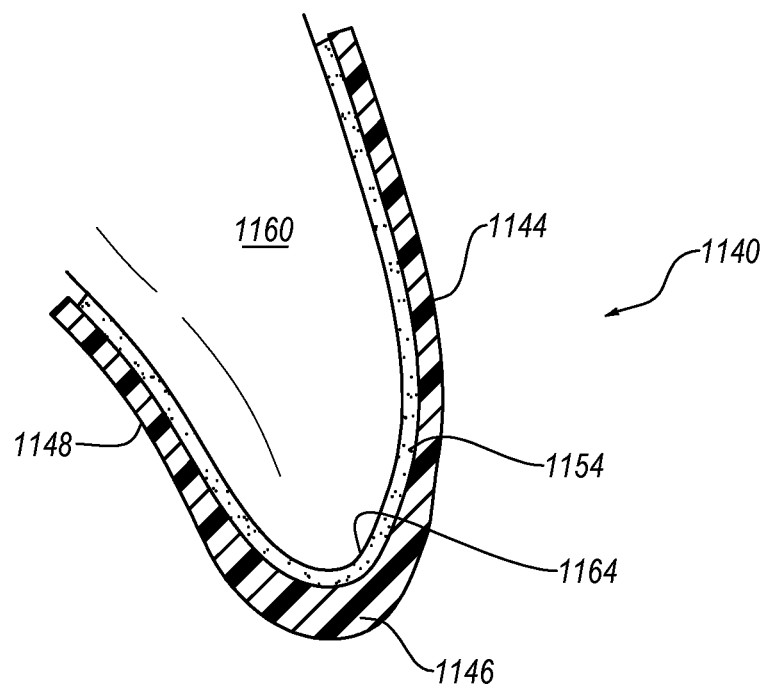
FIG. 11B illustrates an exemplary oral treatment device in use in maintaining an oral treatment composition against an anterior tooth, the treatment device having a thickened occlusial wall.

FIGS. 11A and 11B illustrate exemplary oral treatment devices or trays having a thickened occlusal wall with thinner labial and lingual walls. FIG. 11A illustrates an oral treatment device or barrier 1100 comprising a labial wall 1104, a thickened occlusal wall 1106 extending laterally (e.g., lingually) from labial wall 1104, and a lingual wall 1108 extending laterally (e.g., occlusally-gingivally) from occlusal wall 1106. Oral treatment device or barrier 1100 is shown installed over a tooth 1120, with an oral treatment composition 1114 positioned between oral treatment device or barrier 1100 and tooth 1120. Occlusal wall 1106 includes a V-shaped protrusion 1116 to better approximate the anatomy of tooth 1120, particularly with respect to recess 1122 in an occlusal surface 1124 of tooth 1120. The V-shaped protrusion 1116 provides closer proximity between occlusal wall 1106 and occlusal surface 1124 of tooth 1120. When a user closes his/her mouth and brings posterior teeth in close contact, pressure between opposing occlusal tooth surfaces of corresponding teeth is less likely to move oral treatment device or barrier 1100 out of proper position relative to tooth 1120 (e.g., as a result of occlusal wall 1106 being pushed more deeply into recess 1122 so as to pull labial wall 1104 and/or lingual wall 1108 downward relative to tooth 1120).

FIG. 11B illustrates an oral treatment device or barrier 1140 comprising a labial wall 1144, a thickened occlusal wall 1146 extending laterally (e.g., lingually) from labial wall 1144, and a lingual wall 1148 extending laterally (e.g., occlusally-gingivally) from occlusal wall 1146. Oral treatment device or barrier 1140 is shown installed over a tooth 1160, with an oral treatment composition 1154 positioned between oral treatment device or barrier 1140 and tooth 1160. Thickened occlusal wall 1146 has a thicker cross section than labial wall 1144 and lingual wall 1148 to provide a greater quantity of deformable and/or protective wax-based material in the vicinity of occlusal edge or surface 1164 of tooth 1160. The greater quantity of wax-based material in occlusal wall 1146 resists perforation when occlusal edge or surface 1164 of tooth 1160 makes contact with a secondary surface, such as an opposing occlusal edge of a corresponding tooth or an object placed in a person's mouth.

Figure 12:
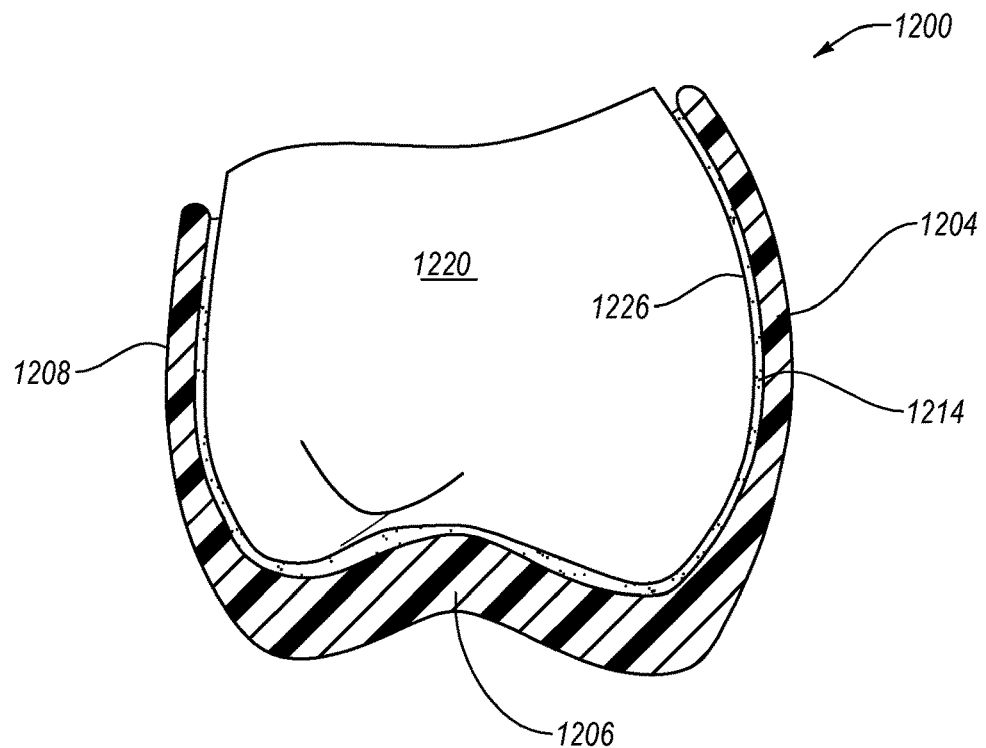
FIG. 12 is a cross-section view of an exemplary oral treatment device having a labial wall with a curvature that corresponds to a facial surface of the tooth.

FIG. 12 illustrates an oral treatment device or barrier 1200 comprising a labial wall 1204, a thickened occlusal wall 1206 extending laterally (e.g., lingually) from labial wall 1204, and a lingual wall 1208 extending laterally (e.g., occlusally-gingivally) from occlusal wall 1206. Oral treatment device or barrier 1200 is shown installed over a tooth 1220, with an oral treatment composition 1214 positioned between oral treatment device or barrier 1200 and tooth 1220. Labial wall 1204 has an enhanced curvature that better approximates the anatomy of tooth 1220, particularly with respect to the curvature of facial surface 1226 of tooth 1220. The enhanced curvature of labial wall 1204 provides closer proximity and better fit between labial wall 1204 and facial surface 1226 of tooth 1220. This, in turn, helps retain oral treatment device 1200 in proper position relative to tooth 1220 and resist dislodgement or slippage of treatment device 1200 that may otherwise result from compressive and/or lateral forces applied to labial wall 1204 during use (e.g., by a person's lip or cheek).

Figure 13:
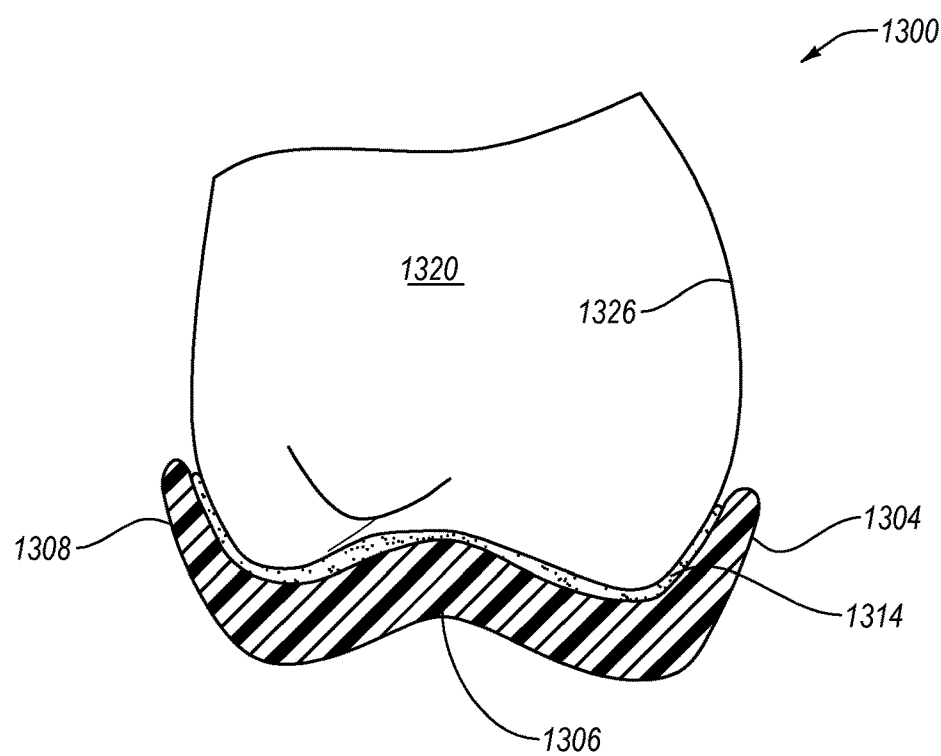
FIG. 13 is a cross-section view of an exemplary oral treatment device having labial and lingual walls that only cover a portion of a patient's teeth.

FIG. 13 illustrates an oral treatment device or barrier 1300 comprising a labial wall 1304, a thickened occlusal wall 1306 extending laterally (e.g., lingually) from labial wall 1304, and a lingual wall 1308 extending laterally (e.g., occlusally-gingivally) from occlusal wall 1306. In this embodiment, labial wall 1304 and lingual wall 1308 only cover part of a patient's teeth (e.g., so as to provide a desired barrier or protection region while minimizing intrusiveness of the device. Oral treatment device or barrier 1300 is shown installed over a portion of tooth 1320.

Alternatively, oral treatment devices (not shown) can have the labial wall that extends beyond the gingival margin and have a curvature at least partially corresponding to a curvature of a labial surface of the skeletal maxilla or alveolar ridge so as to improve fit between the dental treatment device and a person's dental arch when worn.

V. Examples

Following are examples of wax-based compositions that may be used to manufacture oral treatment devices, including dental treatment trays and strip-like barrier layers. The exemplary formulations and manufacturing conditions are given by way of example, and not by limitation. Unless otherwise indicated, all percentages are by weight.

COMPARATIVE EXAMPLE

A sheet of Parafilm® M was thermoformed into a dental treatment tray by heating the sheet to a softening temperature and then vacuum forming the softened sheet over a die having the shape of the dental treatment tray. The resulting dental treatment tray was able to maintain its shape as a tray at room temperature and could be used as a barrier layer in an oral treatment tray. However, the tray lacked thermal stability and lost dimensional stability at temperatures of about 100° F. (about 38° C.) or above. As a result, it was determined that dental treatment trays made by thermoforming Parafilm® M were unsuitable for use in manufacturing oral treatment devices that are subjected to higher temperatures during shipping and storage (i.e., up to 50° C.).

The dental trays in the following Examples were or are manufactured by injection molding a wax-based composition as described below. The wax-based composition of each example was or is initially formed by introducing the materials into a twin screw extruder having multiple zones, heating and mixing the materials in the extruder, extruding the composition into a strand, cooling the extruded strand in a water bath, and chopping the strand in to pellets. The pellets were or are then fed into an injection molding machine and injection molded into dental trays. The injection molding machine was configured to initially heat the wax-based composition prior to introduction into the mold cavity and then cool the material to form the solidified trays. The injection molded trays had an average sidewall thickness of about 0.007-0.008 mil (about 0.18-0.2 mm), with thickened occlusal surfaces of about 0.010-0.013 mils (25-33 mm).

Examples 1-10

| Component | Example | | | | | | | | | |
|---|---|---|---|---|---|---|---|---|---|---|
| | 1 | 2 | 3 | 4 | 5 | 6 | 7 | 8 | 9 | 10 |
| Parafilm ® M[1] | 100% | 35% | 30% | 50% | 90% | 95% | 25% | 25% | 25% | 25% |
| Paraffin wax (mp = 167° F.) | | 65% | | | | | 65% | 65% | 65% | 65% |
| Paraffin wax (mp = 149° F.) | | | 70% | | | | | | | |
| Paraffin wax (mp = 181° F.) | | | | 50% | | | | | | |

-continued

| Component | Example | | | | | | | | | |
|---|---|---|---|---|---|---|---|---|---|---|
| | 1 | 2 | 3 | 4 | 5 | 6 | 7 | 8 | 9 | 10 |
| Thermoplastic polyolefin elastomer | | | | | 10% | 5% | | | | |
| Distilled wax² | | | | | | | 10% | | | |
| Distilled wax³ | | | | | | | | 10% | | |
| Distilled wax⁴ | | | | | | | | | 10% | |
| Distilled wax⁵ | | | | | | | | | | 10% |

[1]Proprietary blend of paraffin wax and polyolefin.
[2]Congealing point: 129.5-135.1° C.; start to open point: 115.6-121.2° C.; terminal point: 129.5-135.1° C.; volume of expansion: 16-18%; travel: 6.37-6.89 mm
[3]Congealing point: 124-129.5° C.; start to open point: 107.3-112.9° C.; terminal point: 126.8-132.3° C.; volume of expansion: 16-18%; travel: 6.37-6.89 mm
[4]Congealing point: 105.1-106.2° C.; start to open point: 98.4-100.0° C.; terminal point: 114.5-116.2° C.; volume of expansion: 14-16%; travel: 5.88-6.37 mm
[5]Congealing point: 100-101.2° C.; start to open point: 89.0-90.1° C.; terminal point: 105.6-106.8° C.; volume of expansion: 14-16%; travel: 5.88-6.37 mm Dental treatment trays made according to Examples 1-10 had varying levels of thermal stability, plastic deformability, and comfort. All had better thermal stability compared to the thermoformed tray of the Comparative Example, even the injection molded tray of Example 1, which was made by injection molding the composition of Parafilm® M. By way of comparison, the tray of Example 1, made by injection molding 100% Parafilm® M, was dimensionally stabile up to a temperature of about 50-52° C. As the amount of Parafilm® M was reduced and replaced by other components, such as paraffin wax, thermoplastic polyolefin elastomer and/or distilled wax, the temperature stability of the trays increased as did the ability of the trays to be plastically deformable in a user's mouth.

Examples 11-19

| Component | Example | | | | | | | | |
|---|---|---|---|---|---|---|---|---|---|
| | 11 | 12 | 13 | 14 | 15 | 16 | 17 | 18 | 19 |
| Parafilm ® M¹ | 25% | 25% | 25% | 25% | 25% | 25% | 25% | 25% | 25% |
| Paraffin Wax (mp = 167° F.) | | 65% | 65% | 65% | 65% | 64% | 65% | 64% | 65% |
| Distilled wax² | | | | | 5% | 8% | | | |
| Distilled wax³ | | | 5% | 5% | 5% | 3% | 5% | 3% | |
| Distilled wax⁴ | | | | 5% | | | | | |
| Distilled wax⁵ | | | | | 5% | | | 5% | 8% |
| Distilled wax⁶ | | 10% | | | | | | | |
| Distilled wax⁷ | | | | | | | | | 10% |

[1]Proprietary blend of paraffin wax and polyolefin.
[2]Congealing point: 129.5-135.1° C.; start to open point: 115.6-121.2° C.; terminal point: 129.5-135.1° C.; volume of expansion: 16-18%; travel: 6.37-6.89 mm
[3]Congealing point: 124-129.5° C.; start to open point: 107.3-112.9° C.; terminal point: 126.8-132.3° C.; volume of expansion: 16-18%; travel: 6.37-6.89 mm
[4]Congealing point: 100-101.2° C.; start to open point: 89.0-90.1° C.; terminal point: 105.6-106.8° C.; volume of expansion: 14-16%; travel: 5.88-6.37 mm
[5]Congealing point: 95.1-96.2° C.; start to open point: 89.5-90.6° C.; terminal point: 100.6-101.7° C.; volume of expansion: 14-16%; travel: 5.88-6.37 mm
[6]Congealing point: 80.1-81.2° C.; start to open point: 74.5-75.6° C.; terminal point: 85.6-86.7° C.; volume of expansion: 14-16%; travel: 5.88-6.37 mm
[7]Congealing point: 109-110.6° C.; start to open point: 104-105.6° C.; terminal point: 125.7-127.9° C.; volume of expansion: 15-17%; travel: 6.13-6.63 mm Dental treatment trays made according to Examples 11-19 had varying levels of thermal stability, plastic deformability, and comfort. The trays made according to Examples 11-19 had improved thermal stability compared to the tray of the Comparative Example. Reducing the amount of Parafilm® M and replacing it with other components, such as paraffin wax and/or distilled wax, increased temperature stability and the ability of the trays to be plastically deformable in a user's mouth.

Examples 20-28

| | Example | | | | | | | | |
|---|---|---|---|---|---|---|---|---|---|
| Component | 20 | 21 | 22 | 23 | 24 | 25 | 26 | 27 | 28 |
| Propylene-based elastomer[1] | | 22% | | 20% | 20% | 20% | 15% | 30% | 15% |
| Propylene-based elastomer[2] | 22% | | | | | | | | |
| Propylene-based elastomer[3] | | | 22% | | | | | | |
| Microcrystalline Wax[4] | 44% | 44% | 44% | 80% | 60% | 40% | 55% | 40% | 40% |
| Paraffin Wax[5] | 33% | 33% | 33% | | 20% | 40% | 30% | 30% | 45% |

[1] Density: 0.862 g/cm$^3$; MFR (230° C./2.16 kg): 3.0 g/10 min; ethylene content: 16.0 wt %; durometer hardness (Shore A, 15 sec, 23° C.); 67; flexural modulus (23° C.): 11.4 MPa; tensile set (23° C.): 13%; tensile stress at 100% (23° C.): 2.12 MPa; tensile stress at 300% (23° C.): 2.68 MPa; tensile strength at break (23° C.): 13.9 MPa; elongate at break (23° C.): 860%; tear strength (23° C.): 31.0 kN/m; viscat softening temp: 59.0° C.
[2] Density: 0.861 g/cm$^3$; melt index: 7.4 g/10 min; MFR (230° C./2.16 kg): 18 g/10 min; ethylene content: 15.0 wt %; durometer hardness (Shore A, 15 sec, 23° C.); 61; flexural modulus (23° C.): 11.0 MPa; tensile set (23° C.): 13%; tensile stress at 100% (23° C.): 1.70 MPa; tensile stress at 300% (23° C.): 2.10 MPa; tensile strength at break (23° C.): >7.29 MPa; elongate at break (23° C.): >2000%; tear strength (23° C.): 33.0 kN/m; viscat softening temp: 48.0° C.
[3] Density: 0.874 g/cm$^3$; melt index: 0.90 g/10 min; MFR (230° C./2.16 kg): 2.2 g/10 min; ethylene content: 10.5 wt %; Shore A hardness (23° C.); 85; flexural modulus (23° C.): 60.4 MPa; tensile set (23° C.): 49%; tensile stress at 100% (23° C.): 4.40 MPa; tensile stress at 300% (23° C.): 4.50 MPa; tensile strength at break (23° C.): 17.8 MPa; elongate at break (23° C.): 1800%; tear strength (23° C.): 64 kN/m; viscat softening temp: 70.0° C.; peak crystallization temp: 65.0° C.; crystallinity, Hf: 28.0 J/g; crystallization peak, Tc: 64° C.
[4] Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max
[5] Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927

Dental treatment trays made according to Examples 20-28 provided improved thermal stability and plastic deformation compared to the tray made according to the Comparative Example.

Examples 29-38

| | Example | | | | | | | | | |
|---|---|---|---|---|---|---|---|---|---|---|
| Component | 29 | 30 | 31 | 32 | 33 | 34 | 35 | 36 | 37 | 38 |
| Propylene-based elastomer[1] | 20% | 20% | 20% | 40% | 30% | 30% | 30% | 35% | 25% | 15% |
| Microcrystalline Wax[2] | 40% | 60% | 20% | 30% | 35% | 50% | 20% | 33% | 38% | 43% |
| Paraffin Wax[3] | 40% | 20% | 60% | 30% | 35% | 20% | 50% | 33% | 38% | 43% |

[1] Density: 0.861 g/cm$^3$; melt index: 7.4 g/10 min; MFR (230° C./2.16 kg): 18 g/10 min; ethylene content: 15.0 wt %; durometer hardness (Shore A, 15 sec, 23° C.); 61; flexural modulus (23° C.): 11.0 MPa; tensile set (23° C.): 13%; tensile stress at 100% (23° C.): 1.70 MPa; tensile stress at 300% (23° C.): 2.10 MPa; tensile strength at break (23° C.): >7.29 MPa; elongate at break (23° C.)
[2] Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max
[3] Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927

Dental treatment trays made according to Examples 29-38 provided improved thermal stability and plastic deformation compared to the tray made according to the Comparative Example.

Examples 39-48

| | Example | | | | | | | | | |
|---|---|---|---|---|---|---|---|---|---|---|
| Component | 39 | 40 | 41 | 42 | 43 | 44 | 45 | 46 | 47 | 48 |
| Thermoplastic elastomer[1] | 20% | 20% | 20% | 40% | 30% | 30% | 30% | 35% | 25% | 22% |

-continued

|  | Example | | | | | | | | | |
|---|---|---|---|---|---|---|---|---|---|---|
| Component | 39 | 40 | 41 | 42 | 43 | 44 | 45 | 46 | 47 | 48 |
| Microcrystalline Wax[2]) | 40% | 60% | 20% | 30% | 35% | 50% | 20% | 33% | 38% | 39% |
| Paraffin Wax[3] | 40% | 20% | 60% | 30% | 35% | 20% | 50% | 33% | 38% | 39% |

[1]Specific Gravity: 885; density: 0.883 g/cm$^3$; MFR (190° C./2.16 kg): 31 g/10 min; durometer hardness (Shore A, 5 sec): 50; tensile stress (100% strain): 1.54 MPa; tensile stress (300% strain): 2.27 MPa; tensile strength (yield): 6.85 MPa; tensile elongation (break): 800%; tear strength (Die C): 23.6 kN/m; melt viscosity (374° F., 200 sec$^{-1}$): 136 Pa-s.
[2]Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max
[3]Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927

Dental treatment trays made according to Examples 39-48 provided improved thermal stability and plastic deformation compared to the tray made according to the Comparative Example.

Examples 49-58

|  | Example | | | | | | | | | |
|---|---|---|---|---|---|---|---|---|---|---|
| Component | 49 | 50 | 51 | 52 | 53 | 54 | 55 | 56 | 57 | 58 |
| Thermoplastic elastomer[1] | 20% | 20% | 20% | 40% | 30% | 30% | 30% | 35% | 25% | 22% |
| Microcrystalline Wax[3]) | 40% | 60% | 20% | 30% | 35% | 50% | 20% | 33% | 38% | 39% |
| Paraffin Wax[4] | 40% | 20% | 60% | 30% | 35% | 20% | 50% | 33% | 38% | 39% |

[1]Density: 0.890 g/cm$^3$; tensile stress (yield): 10.6 MPa; tensile elongation: 780%; tear strength 16 kN/m; compression set (23° C.): 18%; compression set (70° C.): 35%; compression set (100° C.): 52%; Shore A hardness: 60
[2]Drop melt point: 88.9° C. min; kinematic viscosity (100° C.): 16.5 cSt min; oil content: 1.8 wt % max; flash point: 260° C.; ASTM color: 0.5 max; odor: 2 max; needle penetration (25° C.): 10 dmm max
[3]Congealing point: 66.7-74.4° C.; kinematic viscosity (100° C.): 5.7-7.9 cSt; oil content: 1.0 wt % max; saybolt color: +25 min; needle penetration (25° C.): 18 dmm max; specific gravity (25° C.): 0.927

Dental treatment trays made according to Examples 49-58 provided improved thermal stability and plastic deformation compared to the tray made according to the Comparative Example.

Example 59

Any of the compositions of Examples 2-58 is extruded or otherwise formed into a sheet having a thickness so as to be thermoformable and then formed into a tray using a thermoforming technique known in the art. The trays formed according to Example 59 provide improved thermal stability and plastic deformation compared to the tray made according to the Comparative Example.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An oral treatment device, comprising:
   a wax-based composition having a three-dimensional form selected from a therapeutic tray, anti-bruxing tray, treatment tray for temporomandibular joint disorder (TMJ), sports mouth guard, sports mouth guard insert, orthodontic guard tray, post-surgical oral protection device, and deformable device for registering occlusal points of a patient's teeth,
   wherein the wax-based composition is comprised of:
   50% to 95% by weight of a wax component; and
   a thermoplastic elastomer component.

2. The oral treatment device of claim 1, wherein the wax component comprises at least one petroleum wax selected from paraffin wax, intermediate wax, and microcrystalline wax.

3. The oral treatment device of claim 1, the three-dimensional form comprising at least one sidewall and a bottom wall adjacent to and extending laterally from the at least one sidewall.

4. The oral treatment device of claim 1, wherein the oral treatment device comprises a thickened occlusal wall configured to contact an occlusal edge or surface of one or more teeth and thinner labial and lingual walls adjacent to the thickened occlusal wall.

5. The oral treatment device of claim 1, wherein the oral treatment device is thermally stable to a temperature of at least 45° C. and plastically deformable at a temperature of 25° C.

6. The oral treatment device of claim 1, wherein the wax component comprises 60% to 93% by weight of the wax-based composition.

7. The oral treatment device of claim 1, wherein the wax component comprises 70% to 90% by weight of the wax-based composition.

8. The oral treatment device of claim 1, wherein the thermoplastic elastomer component is included in a range of 5% to 50% by weight of the wax-based composition.

9. The oral treatment device of claim 1, wherein the thermoplastic elastomer component is included in a range of 7% to 40% by weight of the wax-based composition.

10. The oral treatment device of claim 1, wherein the thermoplastic elastomer component comprises an olefin-based elastomer.

11. The oral treatment device of claim 10, wherein the olefin-based elastomer is selected from ethylene-, propylene-, and butylene-based elastomers.

12. The oral treatment device of claim 1, further comprising an oral treatment composition adjacent to or impregnated within the three-dimensional form.

13. A kit for providing oral treatment, comprising:
the oral treatment device of claim 1; and
an oral treatment composition initially separate from the three-dimensional form.

14. A method of manufacturing an oral treatment device, comprising:
combining a wax component and a thermoplastic elastomer component to form a mixture comprising 50% to 95% by weight of the wax component;
processing the mixture to form a wax-based composition comprised of the wax component blended with the thermoplastic elastomer component; and
forming the wax-based composition into a three-dimensional form selected from a therapeutic tray, anti-bruxing tray, treatment tray for TMJ, sports mouth guard, sports mouth guard insert, orthodontic guard tray, post-surgical oral protection device, and deformable device for registering occlusal points of a patient's teeth.

15. The method of claim 14, wherein the wax component comprises at least one petroleum wax selected from paraffin wax, intermediate wax, and microcrystalline wax.

16. The method of claim 14, wherein processing includes heating the mixture to a temperature in a range of 50° C. to 225° C. and applying pressure to the mixture in a range 1000 psi to 30,000 psi.

17. The method of claim 14, wherein the wax component and the thermoplastic elastomer component are combined and processed using an extruder.

18. The method of claim 17, wherein the extruder forms the wax-based composition into a sheet, the method further comprising shaping the sheet into the three-dimensional form.

19. The method of claim 17, wherein the extruder forms the wax-based composition into a strand, the method further comprising cutting the strand into pellets and injection molding the pellets into the three-dimensional form.

20. A method for providing oral treatment, comprising:
obtaining an oral treatment device comprising:
a wax-based composition having a three-dimensional form selected from a therapeutic tray, anti-bruxing tray, treatment tray for TMJ, sports mouth guard, sports mouth guard insert, orthodontic guard tray, post-surgical oral protection device, and deformable device for registering occlusal points of a patient's teeth, wherein the wax-based composition is comprised of:
50% to 95% by weight of a wax component; and
a thermoplastic elastomer component; and
performing oral treatment using the oral treatment device.

* * * * *